United States Patent
Sims et al.

(10) Patent No.: US 9,982,229 B2
(45) Date of Patent: May 29, 2018

(54) USE OF HYDROPHOBINS TO INCREASE GAS TRANSFER IN AEROBIC FERMENTATION PROCESSES

(71) Applicant: DANISCO US INC., Palo Alto, CA (US)

(72) Inventors: Evan Sims, San Francisco, CA (US); Michael W. Schelle, San Francisco, CA (US); Gopal Chotani, Cupertino, CA (US)

(73) Assignee: DANISCO US INC., Palo Alto, CA (US)

( * ) Notice: Subject to any disclaimer, the term of this patent is extended or adjusted under 35 U.S.C. 154(b) by 0 days. days.

(21) Appl. No.: 15/102,486

(22) PCT Filed: Nov. 14, 2014

(86) PCT No.: PCT/US2014/065755
§ 371 (c)(1),
(2) Date: Jun. 7, 2016

(87) PCT Pub. No.: WO2015/094527
PCT Pub. Date: Jun. 25, 2015

(65) Prior Publication Data
US 2016/0312178 A1    Oct. 27, 2016

Related U.S. Application Data

(60) Provisional application No. 61/918,543, filed on Dec. 19, 2013.

(51) Int. Cl.
| | | |
|---|---|---|
| *C12N 1/38* | (2006.01) |
| *C12N 1/12* | (2006.01) |
| *C12N 1/14* | (2006.01) |
| *C12N 1/20* | (2006.01) |
| *C12N 1/34* | (2006.01) |
| *C07K 14/37* | (2006.01) |
| *C12P 21/02* | (2006.01) |
| *C12N 9/00* | (2006.01) |
| *C12P 5/00* | (2006.01) |
| *C12P 7/06* | (2006.01) |
| *C12P 7/16* | (2006.01) |
| *C12P 7/18* | (2006.01) |
| *C12P 7/54* | (2006.01) |
| *C12N 5/071* | (2010.01) |

(52) U.S. Cl.
CPC ............... *C12N 1/38* (2013.01); *C07K 14/37* (2013.01); *C12N 1/12* (2013.01); *C12N 1/14* (2013.01); *C12N 1/20* (2013.01); *C12N 1/34* (2013.01); *C12N 5/0682* (2013.01); *C12N 9/00* (2013.01); *C12P 5/007* (2013.01); *C12P 7/06* (2013.01); *C12P 7/16* (2013.01); *C12P 7/18* (2013.01); *C12P 7/54* (2013.01); *C12P 21/02* (2013.01); *Y02E 50/10* (2013.01); *Y02E 50/17* (2013.01)

(58) Field of Classification Search
None
See application file for complete search history.

(56) References Cited

U.S. PATENT DOCUMENTS

2012/0252066 A1* 10/2012 Heng .................. C12P 19/44
435/69.1

OTHER PUBLICATIONS

Zhang X. et al. Adsorption Behavior of Hydrophobin and Hydrophobin/Surfactant Mixtures at the Air-Water Interface. Langmuir 27(18)11316-11323, Sep. 20, 2011.*
Burke J. et al. Interfacial Rheology and Stability of Air Bubbles Stabilized by Mixtures of Hydrophobin and Beta Casein. Food Hydrocolloids 34(1)119-127, Jan. 2014. (Year: 2014).*
Alexandrov N. et al. Interfacial Layers From the Protein HFBII Hydrophobin. J of Colloid and Interface Science 376(1)296-306, Mar. 2012.*

* cited by examiner

*Primary Examiner* — Ralph J Gitomer

(57) ABSTRACT

The present disclosure provides methods, compositions and apparatuses for increasing gas transfer in fermentation processes.

22 Claims, 13 Drawing Sheets

FIGURE 3

SEQ ID NO:1

| | |
|---|---|
| cacattcact caactcctct ttctcaactc tccaaacaca aacattcttt gttgaatacc | 60 |
| aaccatcacc acctttcaag atgcagttct tcgccgtcgc cctcttcgcc accagcgccc | 120 |
| tggctgctgt ctgccctacc ggcctcttct ccaaccctct gtgctgtgcc accaacgtcc | 180 |
| tcgacctcat tggcgttgac tgcaagaccc gtatgttgaa ttccaatctc tgggcatcct | 240 |
| gacattggac gatacagttg acttacacga tgctttacag ctaccatcgc cgtcgacact | 300 |
| ggcgccatct tccaggctca ctgtgccagc aagggctcca agcctctttg ctgcgttgct | 360 |
| cccgtggtaa gtagtgctcg caatggcaaa gaagtaaaaa gacatttggg cctgggatcg | 420 |
| ctaactcttg atatcaaggc cgaccaggct ctcctgtgcc agaaggccat cggcaccttc | 480 |
| taaagcaatg gcttgcttta ctgccggcag tctttgagaa ctctgggctc acaaaagacg | 540 |
| acttgcatgt atcatggggg ctcgcaaatg ggaggatttg gaggggattg aggctgggtt | 600 |
| tggcctatta gaggattgca taatggaaga tttgcgagca ggacatagac gtatctagag | 660 |
| ttctagt | 667 |

FIGURE 4

SEQ ID NO:2

Met Gln Phe Phe Ala Val Ala Leu Phe Ala Thr Ser Ala Leu Ala Ala
1               5                   10                  15

Val Cys Pro Thr Gly Leu Phe Ser Asn Pro Leu Cys Cys Ala Thr Asn
            20                  25                  30

Val Leu Asp Leu Ile Gly Val Asp Cys Lys Thr Pro Thr Ile Ala Val
        35                  40                  45

Asp Thr Gly Ala Ile Phe Gln Ala His Cys Ala Ser Lys Gly Ser Lys
    50                  55                  60

Pro Leu Cys Cys Val Ala Pro Val Ala Asp Gln Ala Leu Leu Cys Gln
 65                  70                  75                  80

Lys Ala Ile Gly Thr Phe
            85

FIGURE 5A

SEQ ID NO:3

| | |
|---|---|
| tttgtatggc tggatctcga aaggcccttg tcatcgccaa gcgtggctaa tatcgaatga | 60 |
| gggacaccga gttgcatatc tcctgatcat tcaaacgaca agtgtgaggt aggcaatcct | 120 |
| cgtatcccat tgctgggctg aaagcttcac acgtatcgca taagcgtctc caaccagtgc | 180 |
| ttaggtgacc cttaaggata cttacagtaa gactgtatta agtcagtcac tctttcactc | 240 |
| gggctttgaa tacgatcctc aatactcccg ataacagtaa gaggatgata cagcctgcag | 300 |
| ttggcaaatg taagcgtaat taaactcagc tgaacggccc ttgttgaaag tctctctcga | 360 |
| tcaaagcaaa gctatccaca gacaagggtt aagcaggctc actcttccta cgccttggat | 420 |
| atgcagcttg gccagcatcg cgcatggcca atgatgcacc cttcacggcc caacggatct | 480 |
| cccgttaaac tcccctgtaa cttggcatca ctcatctgtg atcccaacag actgagttgg | 540 |
| gggctgcggc tggcggatgt cggagcaaag gatcacttca agagcccaga tccggttggt | 600 |
| ccattgccaa tggatctaga ttcggcacct tgatctcgat cactgagaca tggtgagttg | 660 |
| cccggacgca ccacaactcc ccctgtgtca ttgagtcccc atatgcgtct tctcagcgtg | 720 |
| caactctgag acggattagt cctcacgatg aaattaactt ccagcttaag ttcgtagcct | 780 |
| tgaatgagtg aagaaatttc aaaaacaaac tgagtagagg tcttgagcag ctggggtggt | 840 |
| acgcccctcc tcgactcttg ggacatcgta cggcagagaa tcaacggatt cacacctttg | 900 |
| ggtcgagatg agctgatctc gacagatacg tgcttcacca cagctgcagc tacctttgcc | 960 |
| caaccattgc gttccaggat cttgatctac atcaccgcag cacccgagcc aggacggaga | 1020 |
| gaacaatccg gccacagagc agcaccgcct tccaactctg ctcctggcaa cgtcacacaa | 1080 |
| cctgatatta gatatccacc tgggtgattg ccattgcaga gaggtggcag ttggtgatac | 1140 |
| cgactggcca tgcaagacgc ggccgggcta gctgaaatgt ccccgagagg acaattggga | 1200 |
| gcgtctatga cggcgtggag acgacgggaa aggactcagc cgtcatgttg tgttgccaat | 1260 |
| ttgagattgt tgaccgggaa aggggggacg aagaggatgg ctgggtgagg tggtattggg | 1320 |
| aggatgcatc attcgactca gtgagcgatg tagagctcca agaatataaa tatcccttct | 1380 |
| ctgtcttctc aaaatctcct tccatcttgt ccttcatcag caccagagcc agcctgaaca | 1440 |
| cctccagtca acttccctta ccagtacatc tgaatcaaca tccattcttt gaaatctcac | 1500 |

FIGURE 5B cacaaccacc atcttcttca aaatgaagtt cttcgccatc gccgctctct ttgccgccgc     1560
tgccgttgcc cagcctctcg aggaccgcag caacggcaac ggcaatgttt gccctcccgg    1620
cctcttcagc aaccccagt gctgtgccac ccaagtcctt ggcctcatcg gccttgactg     1680
caaagtccgt aagttgagcc ataacataag aatcctcttg acggaaatat gccttctcac    1740
tcctttaccc ctgaacagcc tcccagaacg tttacgacgg caccgacttc cgcaacgtct    1800
gcgccaaaac cggcgcccag cctctctgct gcgtggcccc cgttgtaagt tgatgcccca   1860
gctcaagctc cagtctttgg caaacccatt ctgacaccca gactgcaggc cggccaggct    1920
cttctgtgcc agaccgccgt cggtgcttga gatgcccgcc cggggtcaag gtgtgcccgt    1980
gagaaagccc acaaagtgtt gatgaggacc atttccggta ctgggaaagt tggctccacg    2040
tgtttgggca ggtttgggca agttgtgtag atattccatt cgtacgccat tcttattctc    2100
caatatttca gtacactttt cttcataaat caaaaagact gctattctct ttgtgacatg    2160
ccggaaggga acaattgctc ttggtctctg ttatttgcaa gtaggagtgg gagattcgcc    2220
ttagagaaag tagagaagct gtgcttgacc gtggtgtgac tcgacgagga tggactgaga    2280
gtgttaggat taggtcgaac gttgaagtgt atacaggatc gtctggcaac ccacggatcc    2340
tatgacttga tgcaatggtg aagatgaatg acagtgtaag aggaaaagga aatgtccgcc    2400
ttcagctgat atccacgcca atgatacagc gatatacctc caatatctgt gggaacgaga    2460
catgacatat ttgtgggaac aacttcaaac agcgagccaa gacctcaata tgcacatcca    2520
aagccaaaca ttggcaagac gagagacagt cacattgtcg tcgaaagatg gcatcgtacc    2580
caaatcatca gctctcatta tcgcctaaac cacagattgt ttgccgtccc ccaactccaa    2640
aacgttacta caaaagacat gggcgaatgc aaagacctga agcaaaccc tttttgcgac    2700 tcaattccct cctttgtcct cggaatgatg atccttcacc aagtaaaaga aaagaagat    2760 tgagataata catgaaaagc acaacggaaa cgaaagaacc aggaaaagaa taaatctatc    2820
acgcaccttg tccccacact aaaagcaaca gggggggtaa aatgaaat                2868

FIGURE 6

SEQ ID NO:4

Met Lys Phe Phe Ala Ile Ala Ala Leu Phe Ala Ala Ala Ala Val Ala
1               5                   10                  15

Gln Pro Leu Glu Asp Arg Ser Asn Gly Asn Gly Asn Val Cys Pro Pro
            20                  25                  30

Gly Leu Phe Ser Asn Pro Gln Cys Cys Ala Thr Gln Val Leu Gly Leu
        35                  40                  45

Ile Gly Leu Asp Cys Lys Val Pro Ser Gln Asn Val Tyr Asp Gly Thr
    50                  55                  60

Asp Phe Arg Asn Val Cys Ala Lys Thr Gly Ala Gln Pro Leu Cys Cys
65                  70                  75                  80

Val Ala Pro Val Ala Gly Gln Ala Leu Leu Cys Gln Thr Ala Val Gly Ala
                85                  90                  95

FIGURE 7

SEQ ID NO:5

| | |
|---|---|
| agtcgaacac cccagttcaa ctaccccagc ccttccttcc ttcgctatcc ttccttacaa | 60 |
| cctgctcgcc atgttcgccc gtctccccgt cgtgttcctc tacgccttcg tcgcgttcgg | 120 |
| cgccctcgtc gctgccctcc caggtggcca cccgggcacg acgtacgtcg acctctcacc | 180 |
| gtcctctaat gtcttgctga tgaagccccg tatagcacgc cgccggttac gacgacggtg | 240 |
| acggtgacca cggtgagtag ctttctcgcc gtcgacgact cgaacgcatt ggctaatttt | 300 |
| tgctcatagc cgccctcgac gacgaccatc gccgccggtg gcacgtgtac tacggggtcg | 360 |
| ctctcttgct gcaaccaggt tcaatcggta cgtacatcaa agcggcacga ccaggcatct | 420 |
| cagctgacgg ccacatcgta caggcgagca gcagccctgt taccgccctc ctcggcctgc | 480 |
| tcggcattgt cctcagcgac ctcaacgttc tcgttggcat cagctgctct cccctcactg | 540 |
| tgagatcttt ttgttcactg tcccaattac tgcgcactga cagactttgc caggtcatcg | 600 |
| gtgtcggagg cagcggctgt tcggcgcaga ccgtctgctg cgaaaacacc caattcgtat | 660 |
| gtatactttc catgcgtgtc cctttctccg ctaatcatct gtagaacggg ctgatcaaca | 720 |
| tcggttgcac ccccatcaac atcctctgag caggtgaacg cgcctgtcgg tgggatattc | 780 |
| gggcgacggg agcctcgggc aatctgagcc tcgttactgc ctagcaaatt cggaatccct | 840 |
| tcgatgtcat agggtcgcgg acaagtgatc gtcttgctac atactccaag gtgttgactc | 900 |
| attccctcag ataatgaaca ttgttgttgt tgttgtttgt tctct | 945 |

FIGURE 8

SEQ ID NO: 6

Met Phe Ala Arg Leu Pro Val Val Phe Leu Tyr Ala Phe Val Ala Phe
1               5                   10                  15

Gly Ala Leu Val Ala Ala Leu Pro Gly Gly His Pro Gly Thr Thr Thr
            20                  25                  30

Pro Pro Val Thr Thr Thr Val Thr Val Thr Thr Pro Pro Ser Thr Thr
            35                  40                  45

Thr Ile Ala Ala Gly Gly Thr Cys Thr Thr Gly Ser Leu Ser Cys Cys
        50                  55                  60

Asn Gln Val Gln Ser Ala Ser Ser Ser Pro Val Thr Ala Leu Leu Gly
65                  70                  75                  80

Leu Leu Gly Ile Val Leu Ser Asp Leu Asn Val Leu Val Gly Ile Ser
                85                  90                  95

Cys Ser Pro Leu Thr Val Ile Gly Val Gly Gly Ser Gly Cys Ser Ala
                100                 105                 110

Gln Thr Val Cys Cys Glu Asn Thr Gln Phe Asn Gly Leu Ile Asn Ile
                115                 120                 125

Gly Cys Thr Pro Ile Asn Ile Leu
                130                 135

FIGURE 9

SEQ ID NO: 7

| | |
|---|---|
| atcatcagca tcaacatctt cacttcacaa catcttctca accttccaac tcaccttcca | 60 |
| aaccaccttc aaaaccaact cccagcttct ttcagcaaac ccccaaccgc caaaatgcag | 120 |
| ttcaccagcg tcttcaccat cctcgccatt gccatgaccg ccgctgcggc cccggctgag | 180 |
| gttgttcccc gcgccaccac catcggcccc aacacctgct ccatcgacga ctacaagcct | 240 |
| tactgctgcc agtctatgtc cggccccgcc ggctcccctg gtctcctcaa cctcatcccc | 300 |
| gtcgacctca gcgcctcgct cggctgcgtt gtcggtgtca tcggctccca atgtggtgcc | 360 |
| agcgtcaagt gctgcaagga cgatgttacc aacaccggca actccttcct catcatcaac | 420 |
| gctgccaact gcgttgccta agtgtttacg cggcaacagc gcaaagtcta ggcaatgcct | 480 |
| tgttctcaac gctgctgcca gtccagcacc ccccttctgc agcaaggagc cccttctgc | 540 |
| tggactggca gcacaacgag ctgctactac aacacaagca tcatgcctgg acgcaacaga | 600 |
| agccgataat cttggggttt ggttttgggg gatgaaggtg atgagttgat ggattggatc | 660 |
| gatatcttac aatgcgtgtc tcttcctgtt aagatctgct ttactatttt cctattttct | 720 |
| tttacacata gctatgtatc actaaggcct ggtgattaat acactctctt aaccct | 776 |

FIGURE 10

SEQ ID NO:8

Met Gln Phe Thr Ser Val Phe Thr Ile Leu Ala Ile Ala Met Thr Ala
1               5                   10                  15

Ala Ala Ala Pro Ala Glu Val Val Pro Arg Ala Thr Thr Ile Gly Pro
            20                  25                  30

Asn Thr Cys Ser Ile Asp Asp Tyr Lys Pro Tyr Cys Cys Gln Ser Met
            35                  40                  45

Ser Gly Pro Ala Gly Ser Pro Gly Leu Leu Asn Leu Ile Pro Val Asp
        50                  55                  60

Leu Ser Ala Ser Leu Gly Cys Val Val Gly Val Ile Gly Ser Gln Cys
65                  70                  75                  80

Gly Ala Ser Val Lys Cys Cys Lys Asp Asp Val Thr Asn Thr Gly Asn
                85                  90                  95

Ser Phe Leu Ile Ile Asn Ala Ala Asn Cys Val Ala
            100                 105

FIGURE 11

SEQ ID NO:9

| | |
|---|---:|
| atgaagttcg ccggtgtctt gcttgctgtc gccgctgcgg cgactgccct gccaaacgtc | 60 |
| ggtcccagtg ggaagacggc tcacaagccg caccaggagc ctttctggcc tgtgcagcag | 120 |
| gacgtgaccg tggaacaggc caaggctatc tgtggtgaag caaccaggt cgcttgctgc | 180 |
| aacgaggtca gctacgcggg cgacaccacc gaaatcgcga ccggccccct ggctggcacc | 240 |
| ctcaaggacc tgctcggcgg caagaacggc gccaagggcc tgggtctctt cgacaagtgc | 300 |
| tcgcgtctca atgtcgatct cctgcttggc ctgtcgagcc tcatcaacca agaatgcaag | 360 |
| cagcacattg cctgctgcca gggcaacgag gccgattcct ccaacgacct catcggtctc | 420 |
| aacattcctt gcattgccct tggctcgctg ctg | 453 |

FIGURE 12

SEQ ID NO:10

Met Lys Phe Ala Gly Val Leu Leu Ala Val Ala Ala Ala Ala Thr Ala
1               5                   10                  15

Leu Pro Asn Val Gly Pro Ser Gly Lys Thr Ala His Lys Pro His Gln
            20                  25                  30

Glu Pro Phe Trp Pro Val Gln Gln Asp Val Thr Val Glu Gln Ala Lys
        35                  40                  45

Ala Ile Cys Gly Glu Gly Asn Gln Val Ala Cys Cys Asn Glu Val Ser
    50                  55                  60

Tyr Ala Gly Asp Thr Thr Glu Ile Ala Thr Gly Pro Leu Ala Gly Thr
65                  70                  75                  80

Leu Lys Asp Leu Leu Gly Gly Lys Asn Gly Ala Lys Gly Leu Gly Leu
            85                  90                  95

Phe Asp Lys Cys Ser Arg Leu Asn Val Asp Leu Leu Leu Gly Leu Ser
            100                 105                 110

Ser Leu Ile Asn Gln Glu Cys Lys Gln His Ile Ala Cys Cys Gln Gly
        115                 120                 125

Asn Glu Ala Asp Ser Ser Asn Asp Leu Ile Gly Leu Asn Ile Pro Cys
    130                 135                 140

Ile Ala Leu Gly Ser Leu Leu
145                 150

SEQUENCE LISTING

<160> NUMBER OF SEQ ID NOS: 10

<210> SEQ ID NO 1
<211> LENGTH: 667
<212> TYPE: DNA
<213> ORGANISM: Trichoderma reesei

<400> SEQUENCE: 1

```
cacattcact caactcctct ttctcaactc tccaaacaca acattctttt gttgaatacc      60
aaccatcacc acctttcaag atgcagttct tcgccgtcgc cctcttcgcc accagcgccc     120
tggctgctgt ctgccctacc ggcctcttct ccaaccctct gtgctgtgcc accaacgtcc     180
tcgacctcat tggcgttgac tgcaagaccc gtatgttgaa ttccaatctc tgggcatcct     240
gacattggac gatacagttg acttacacga tgctttacag ctaccatcgc cgtcgacact     300
ggcgccatct tccaggctca ctgtgccagc aagggctcca agcctctttg ctgcgttgct     360
cccgtggtaa gtagtgctcg caatggcaaa gaagtaaaaa gacatttggg cctgggatcg     420
ctaactcttg atatcaaggc cgaccaggct ctcctgtgcc agaaggccat cggcaccttc     480
taaagcaatg gcttgcttta ctgccggcag tctttgaaaa ctctgggctc acaaaagacg     540
acttgcatgt atcatggggg ctcgcaaatg ggaggatttg gaggggattg aggctgggtt     600
tggcctatta gaggattgca taatggaaga tttgcgagca ggacatagac gtatctagag     660
ttctagt                                                               667
```

<210> SEQ ID NO 2
<211> LENGTH: 86
<212> TYPE: PRT
<213> ORGANISM: Trichoderma reesei

<400> SEQUENCE: 2

```
Met Gln Phe Phe Ala Val Ala Leu Phe Ala Thr Ser Ala Leu Ala Ala
1               5                   10                  15

Val Cys Pro Thr Gly Leu Phe Ser Asn Pro Leu Cys Cys Ala Thr Asn
            20                  25                  30

Val Leu Asp Leu Ile Gly Val Asp Cys Lys Thr Pro Thr Ile Ala Val
        35                  40                  45

Asp Thr Gly Ala Ile Phe Gln Ala His Cys Ala Ser Lys Gly Ser Lys
    50                  55                  60

Pro Leu Cys Cys Val Ala Pro Val Ala Asp Gln Ala Leu Leu Cys Gln
65                  70                  75                  80

Lys Ala Ile Gly Thr Phe
                85
```

<210> SEQ ID NO 3
<211> LENGTH: 2868
<212> TYPE: DNA
<213> ORGANISM: Trichoderma reesei

<400> SEQUENCE: 3

```
tttgtatggc tggatctcga aaggcccttg tcatcgccaa gcgtggctaa tatcgaatga      60
gggacaccga gttgcatatc tcctgatcat tcaaacgaca agtgtgaggt aggcaatcct     120
cgtatcccat tgctgggctg aaagcttcac acgtatcgca taagcgtctc caaccagtgc     180
ttaggtgacc cttaaggata cttacagtaa gactgtatta agtcagtcac tctttcactc     240
gggctttgaa tacgatcctc aatactcccg ataacagtaa gaggatgata cagcctgcag     300
ttggcaaatg taagcgtaat taaactcagc tgaacggccc ttgttgaaag tctctctcga     360
```

-continued

| | |
|---|---|
| tcaaagcaaa gctatccaca gacaagggtt aagcaggctc actcttccta cgccttggat | 420 |
| atgcagcttg gccagcatcg cgcatggcca atgatgcacc cttcacgcc caacggatct | 480 |
| cccgttaaac tcccctgtaa cttggcatca ctcatctgtg atcccaacag actgagttgg | 540 |
| gggctgcggc tggcggatgt cggagcaaag gatcacttca agagcccaga tccggttggt | 600 |
| ccattgccaa tggatctaga ttcggcacct tgatctcgat cactgagaca tggtgagttg | 660 |
| cccgacgca ccacaactcc ccctgtgtca ttgagtcccc atatgcgtct ctcagcgtg | 720 |
| caactctgag acggattagt cctcacgatg aaattaactt ccagcttaag ttcgtagcct | 780 |
| tgaatgagtg aagaaatttc aaaaacaaac tgagtagagg tcttgagcag ctggggtggt | 840 |
| acgcccctcc tcgactcttg ggacatcgta cggcagagaa tcaacggatt cacacctttg | 900 |
| ggtcgagatg agctgatctc gacagatacg tgcttcacca cagctgcagc tacctttgcc | 960 |
| caaccattgc gttccaggat cttgatctac atcaccgcag caccgagcc aggacggaga | 1020 |
| gaacaatccg ccacagagc agcaccgcct tccaactctg ctcctggcaa cgtcacacaa | 1080 |
| cctgatatta gatatccacc tgggtgattg ccattgcaga gaggtggcag ttggtgatac | 1140 |
| cgactggcca tgcaagacgc ggccgggcta gctgaaatgt ccccgagagg acaattggga | 1200 |
| gcgtctatga cggcgtggag acgacgggaa aggactcagc cgtcatgttg tgttgccaat | 1260 |
| ttgagattgt tgaccgggaa aggggggacg aagaggatgg ctgggtgagg tggtattggg | 1320 |
| aggatgcatc attcgactca gtgagcgatg tagagctcca agaatataaa tatcccttct | 1380 |
| ctgtcttctc aaaatctcct tccatcttgt ccttcatcag caccagagcc agcctgaaca | 1440 |
| cctccagtca acttcccta ccagtacatc tgaatcaaca tccattcttt gaaatctcac | 1500 |
| cacaaccacc atcttcttca aaatgaagtt cttcgccatc gccgctctct ttgccgccgc | 1560 |
| tgccgttgcc cagcctctcg aggaccgcag caacggcaac ggcaatgttt gccctcccgg | 1620 |
| cctcttcagc aaccccagt gctgtgccac ccaagtcctt ggcctcatcg gccttgactg | 1680 |
| caaagtccgt aagttgagcc ataacataag aatcctcttg acggaaatat gccttctcac | 1740 |
| tcctttaccc ctgaacagcc tcccagaacg tttacgacgg caccgacttc cgcaacgtct | 1800 |
| gcgccaaaac cggcgcccag cctctctgct gcgtggcccc cgttgtaagt tgatgcccca | 1860 |
| gctcaagctc cagtctttgg caaacccatt ctgacaccca gactgcaggc cggccaggct | 1920 |
| cttctgtgcc agaccgccgt cggtgcttga gatgcccgcc cggggtcaag gtgtgcccgt | 1980 |
| gagaaagccc acaaagtgtt gatgaggacc atttccggta ctgggaaagt tggctccacg | 2040 |
| tgtttgggca ggtttgggca agttgtgtag atattccatt cgtacgccat tcttattctc | 2100 |
| caatatttca gtacacttt cttcataaat caaaagact gctattctct ttgtgacatg | 2160 |
| ccggaaggga acaattgctc ttggtctctg ttatttgcaa gtaggagtgg agattcgcc | 2220 |
| ttagagaaag tagagaagct gtgcttgacc gtggtgtgac tcgacgagga tggactgaga | 2280 |
| gtgttaggat taggtcgaac gttgaagtgt atacaggatc gtctggcaac ccacggatcc | 2340 |
| tatgacttga tgcaatggtg aagatgaatg acagtgtaag aggaaaagga aatgtccgcc | 2400 |
| ttcagctgat atccacgcca atgatacagc gatatacctc caatatcgt gggaacgaga | 2460 |
| catgacatat ttgtgggaac aacttcaaac agcgagccaa gacctcaata tgcacatcca | 2520 |
| aagccaaaca ttggcaagac gagagacagt cacattgtcg tcgaaagatg gcatcgtacc | 2580 |
| caaatcatca gctctcatta tcgcctaaac cacagattgt ttgccgtccc ccaactccaa | 2640 |
| aacgttacta caaaagacat gggcgaatgc aaagacctga aagcaaaccc ttttttgcgac | 2700 |

```
tcaattcccc cctttgtcct cggaatgatg atccttcacc aagtaaaaga aaagaagat    2760 tgagataata catgaaaagc acaacggaaa cgaaagaacc aggaaaagaa taaatctatc    2820
acgcaccttg tccccacact aaaagcaaca ggggggggtaa aatgaaat                2868
```

```
<210> SEQ ID NO 4
<211> LENGTH: 97
<212> TYPE: PRT
<213> ORGANISM: Trichoderma reesei

<400> SEQUENCE: 4
```

```
Met Lys Phe Phe Ala Ile Ala Ala Leu Phe Ala Ala Ala Val Ala
1               5                   10                  15

Gln Pro Leu Glu Asp Arg Ser Asn Gly Asn Gly Asn Val Cys Pro Pro
            20                  25                  30

Gly Leu Phe Ser Asn Pro Gln Cys Cys Ala Thr Gln Val Leu Gly Leu
        35                  40                  45

Ile Gly Leu Asp Cys Lys Val Pro Ser Gln Asn Val Tyr Asp Gly Thr
    50                  55                  60

Asp Phe Arg Asn Val Cys Ala Lys Thr Gly Ala Gln Pro Leu Cys Cys
65                  70                  75                  80

Val Ala Pro Val Ala Gly Gln Ala Leu Leu Cys Gln Thr Ala Val Gly
                85                  90                  95

Ala
```

```
<210> SEQ ID NO 5
<211> LENGTH: 945
<212> TYPE: DNA
<213> ORGANISM: Schizophyllum commune

<400> SEQUENCE: 5
```

```
agtcgaacac cccagttcaa ctaccccagc ccttccttcc ttcgctatcc ttccttacaa     60
cctgctcgcc atgttcgccc gtctcccgt cgtgttcctc tacgccttcg tcgcgttcgg    120
cgccctcgtc gctgccctcc caggtggcca cccgggcacg acgtacgtcg acctctcacc    180
gtcctctaat gtcttgctga tgaagccccg tatagcacgc cgccggttac gacgacggtg    240
acggtgacca cggtgagtag cttttctcgcc gtcgacgact cgaacgcatt ggctaatttt    300
tgctcatagc cgccctcgac gacgaccatc gccgccggtg gcacgtgtac tacggggtcg    360
ctctcttgct gcaaccaggt tcaatcggta cgtacatcaa agcggcacga ccaggcatct    420
cagctgacgg ccacatcgta caggcgagca gcagccctgt taccgccctc tcggcctgc    480 tcggcattgt cctcagcgac ctcaacgttc tcgttggcat cagctgctct cccctcactg    540
tgagatcttt tgttcactg tcccaattac tgcgcactga cagactttgc caggtcatcg    600
gtgtcggagg cagcggctgt tcggcgcaga ccgtctgctg cgaaaacacc caattcgtat    660
gtatactttc catgcgtgtc cctttctccg ctaatcatct gtagaacggg ctgatcaaca    720
tcggttgcac cccatcaac atcctctgag caggtgaacg cgcctgtcgg tgggatattc    780
gggcgacggg agcctcgggc aatctgagcc tcgttactgc ctagcaaatt cggaatccct    840
tcgatgtcat agggtcgcgg acaagtgatc gtcttgctac atactccaag gtgttgactc    900
attccctcag ataatgaaca ttgttgttgt tgttgtttgt tctct                    945
```

```
<210> SEQ ID NO 6
<211> LENGTH: 136
<212> TYPE: PRT
<213> ORGANISM: Schizophyllum commune
```

<400> SEQUENCE: 6

Met Phe Ala Arg Leu Pro Val Val Phe Leu Tyr Ala Phe Val Ala Phe
1               5                   10                  15

Gly Ala Leu Val Ala Ala Leu Pro Gly Gly His Pro Gly Thr Thr Thr
            20                  25                  30

Pro Pro Val Thr Thr Val Thr Val Thr Thr Pro Pro Ser Thr Thr
            35                  40                  45

Thr Ile Ala Ala Gly Gly Thr Cys Thr Thr Gly Ser Leu Ser Cys Cys
    50                  55                  60

Asn Gln Val Gln Ser Ala Ser Ser Ser Pro Val Thr Ala Leu Leu Gly
65                  70                  75                  80

Leu Leu Gly Ile Val Leu Ser Asp Leu Asn Val Leu Val Gly Ile Ser
                85                  90                  95

Cys Ser Pro Leu Thr Val Ile Gly Val Gly Ser Gly Cys Ser Ala
            100                 105                 110

Gln Thr Val Cys Cys Glu Asn Thr Gln Phe Asn Gly Leu Ile Asn Ile
            115                 120                 125

Gly Cys Thr Pro Ile Asn Ile Leu
            130                 135

<210> SEQ ID NO 7
<211> LENGTH: 776
<212> TYPE: DNA
<213> ORGANISM: Neurospora crassa

<400> SEQUENCE: 7
atcatcagca tcaacatctt cacttcacaa catcttctca accttccaac tcaccttcca      60
aaccaccttc aaaaccaact cccagcttct ttcagcaaac ccccaaccgc aaaatgcag     120 ttcaccagcg tcttcaccat cctcgccatt gccatgaccg ccgctgcggc cccggctgag     180
gttgttcccc gcgccaccac catcggcccc aacacctgct ccatcgacga ctacaagcct     240
tactgctgcc agtctatgtc cggccccgcc ggctcccctg gtctcctcaa cctcatcccc     300
gtcgacctca gcgcctcgct cggctgcgtt gtcggtgtca tcggctccca atgtggtgcc     360
agcgtcaagt gctgcaagga cgatgttacc aacaccggca actccttcct catcatcaac     420
gctgccaact cgcttgccta agtgtttacg cggcaacagc gcaaagtcta ggcaatgcct     480
tgttctcaac gctgctgcca gtccagcacc ccccttctgc agcaaggagc cccttctgc     540 tggactggca gcacaacgag ctgctactac aacacaagca tcatgcctgg acgcaacaga     600
agccgataat cttggggttt ggttttgggg gatgaaggtg atgagttgat ggattggatc     660
gatatcttac aatgcgtgtc tcttcctgtt aagatctgct ttactatttt cctatttttct     720 tttacacata gctatgtatc actaaggcct ggtgattaat acactctctt aaccct         776

<210> SEQ ID NO 8
<211> LENGTH: 108
<212> TYPE: PRT
<213> ORGANISM: Neurospora crassa

<400> SEQUENCE: 8

Met Gln Phe Thr Ser Val Phe Thr Ile Leu Ala Ile Ala Met Thr Ala
1               5                   10                  15

Ala Ala Ala Pro Ala Glu Val Val Pro Arg Ala Thr Thr Ile Gly Pro
            20                  25                  30

Asn Thr Cys Ser Ile Asp Asp Tyr Lys Pro Tyr Cys Cys Gln Ser Met

```
            35                  40                  45
Ser Gly Pro Ala Gly Ser Pro Gly Leu Leu Asn Leu Ile Pro Val Asp
 50                  55                  60

Leu Ser Ala Ser Leu Gly Cys Val Val Gly Val Ile Gly Ser Gln Cys
 65                  70                  75                  80

Gly Ala Ser Val Lys Cys Cys Lys Asp Asp Val Thr Asn Thr Gly Asn
                 85                  90                  95

Ser Phe Leu Ile Ile Asn Ala Ala Asn Cys Val Ala
                100                 105
```

<210> SEQ ID NO 9
<211> LENGTH: 453
<212> TYPE: DNA
<213> ORGANISM: Talaromyces thermophilus

<400> SEQUENCE: 9

```
atgaagttcg ccggtgtctt gcttgctgtc gccgctgcgg cgactgccct gccaaacgtc    60
ggtcccagtg gaagacggc tcacaagccg caccaggagc ctttctggcc tgtgcagcag   120
gacgtgaccg tggaacaggc caaggctatc tgtggtgaag caaccaggt cgcttgctgc   180 aacgaggtca gctacgcggg cgacaccacc gaaatcgcga ccggccccct ggctggcacc   240
ctcaaggacc tgctcggcgg caagaacggc gccaagggcc tgggtctctt cgacaagtgc   300
tcgcgtctca atgtcgatct cctgcttggc ctgtcgagcc tcatcaacca agaatgcaag   360
cagcacattg cctgctgcca gggcaacgag gccgattcct ccaacgacct catcggtctc   420
aacattcctt gcattgccct tggctcgctg ctg                                453
```

<210> SEQ ID NO 10
<211> LENGTH: 151
<212> TYPE: PRT
<213> ORGANISM: Talaromyces thermophilus

<400> SEQUENCE: 10

```
Met Lys Phe Ala Gly Val Leu Leu Ala Val Ala Ala Ala Thr Ala
 1               5                  10                  15

Leu Pro Asn Val Gly Pro Ser Gly Lys Thr Ala His Lys Pro His Gln
                 20                  25                  30

Glu Pro Phe Trp Pro Val Gln Gln Asp Val Thr Val Glu Gln Ala Lys
             35                  40                  45

Ala Ile Cys Gly Glu Gly Asn Gln Val Ala Cys Cys Asn Glu Val Ser
 50                  55                  60

Tyr Ala Gly Asp Thr Thr Glu Ile Ala Thr Gly Pro Leu Ala Gly Thr
 65                  70                  75                  80

Leu Lys Asp Leu Leu Gly Gly Lys Asn Gly Ala Lys Gly Leu Gly Leu
                 85                  90                  95

Phe Asp Lys Cys Ser Arg Leu Asn Val Asp Leu Leu Gly Leu Ser
                100                 105                 110

Ser Leu Ile Asn Gln Glu Cys Lys Gln His Ile Ala Cys Cys Gln Gly
            115                 120                 125

Asn Glu Ala Asp Ser Ser Asn Asp Leu Ile Gly Leu Asn Ile Pro Cys
130                 135                 140

Ile Ala Leu Gly Ser Leu Leu
145                 150
```

USE OF HYDROPHOBINS TO INCREASE GAS TRANSFER IN AEROBIC FERMENTATION PROCESSES

CROSS REFERENCE TO RELATED APPLICATIONS

This application is the National Stage of International Application No. PCT/US2014/065755, filed Nov. 14, 2014, which claims benefit of priority from U.S. Provisional patent application Ser. No. 61/918,543, filed 19 Dec. 2013, the contents of which are incorporated herein by reference in their entirety.

SEQUENCE LISTING

The sequence listing submitted via EFS, in compliance with 37 C.F.R. § 1.52(e), is incorporated herein by reference. The sequence listing text file submitted via EFS contains the file "NB40411USPCT_SequenceListing.txt" created on Oct. 11, 2016, which is 13.2 KB (13,569 bytes) in size.

BACKGROUND OF THE INVENTION

Aerobic, fed-batch fermentation is a common mode for the culture of industrially important microorganisms for the production of antibiotics, chemicals, biochemicals, enzymes, and other biologically derived products. This mode of operation entails, at the very least, feeding a carbon source to the culture, aeration, usually with air, and some means of mixing the culture to distribute substrate and disperse air bubbles. In most of the fermentation processes, the process requires a strong dispersion of micro-bubbles of air into the media, in order to permit transfer of oxygen and other gases from the bubbles to the micro-organisms.

In the case of stirred-tank reactors, mixing is provided by a combination of one or more impellers or turbines and induced gas circulation currents by the sparging of air into the reactor vessel. In the case of air-lift and bubble-column reactors, mixing is accomplished via the induced currents from the introduction of air into the reactor.

In all cases, gas-liquid mass transfer is a critical factor determining equipment and process performance. Processes that have high oxygen demand require powerful motors and compressors for mechanical agitation and delivery of air, respectively. Therefore, any factor that can make gas-liquid mass transfer more efficient is potentially beneficial because it reduces both variable costs and the capital expense of the reactor equipment.

This present invention provide methods, apparatuses and compositions that could reduce costs associated with oxygen transfer (e.g., electricity for air and mixing) in fermentation processes and/or allow fermentation vessels to operate at higher volumetric productivity. Any system that relies on a fermentation process that operates in a high oxygen transfer regime (e.g. *Bacillus subtilis* or *Trichoderma* fermentation processes) may potentially benefit from the methods, apparatuses and compositions described herein.

SUMMARY OF THE INVENTION

Described are compositions, kits, apparatuses and methods relating to increasing gas transfer in a fermentation process.

Aspects and embodiments of the compositions, kits, apparatuses and methods are set forth in the following separately numbered paragraphs.

1. A method of increasing gas transfer in an aerobic fermentation process comprising adding one or more hydrophobins to a fermentation medium.

2. The method of paragraph 1, where the gas is oxygen.

3. The method of paragraphs 1 or 2, wherein at least one of the one or more hydrophobins is a hydrophobin having the general formula (I):

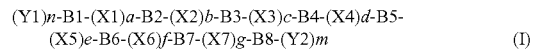

$(Y1)_n$-B1-$(X1)_a$-B2-$(X2)_b$-B3-$(X3)_c$-B4-$(X4)_d$-B5-$(X5)_e$-B6-$(X6)_f$-B7-$(X7)_g$-B8-$(Y2)_m$ (I)

wherein:
m and n are independently an integer between 0 to 2000;
B1, B2, B3, B4, B5, B6, B7 and B8 are each an amino acid independently selected from the group consisting of Cys, Leu, Ala, Pro, Ser, Thr, Met or Gly, at least 6 of the residues B1 through B8 being Cys;
X1, X2, X3, X4, X5, X6, X7, Y1 and Y2 independently represent any amino acid;
a is an integer between 1 to 50;
b is an integer between 0 to 5;
c is an integer between 1 to 100;
d is an integer between 1 to 100;
e is an integer between 1 to 50;
f is an integer between 0 to 5; and
g is an integer between 1 to 100.

4. The method according to any preceding paragraph, wherein the hydrophobin has a sequence of between 40 and 120 amino acids in length in the hydrophobin core.

5. The method according to any preceding paragraph, wherein at least one of the one or more hydrophobins has the general formula (II):

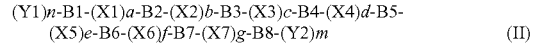

$(Y1)_n$-B1-$(X1)_a$-B2-$(X2)_b$-B3-$(X3)_c$-B4-$(X4)_d$-B5-$(X5)_e$-B6-$(X6)_f$-B7-$(X7)_g$-B8-$(Y2)_m$ (II)

wherein:
m and n are independently an integer between 0 to 20;
B1, B2, B3, B4, B5, B6, B7 and B8 are each an amino acid independently selected from the group consisting of Cys, Leu, Ala, Pro, Ser, Thr, Met or Gly, at least 7 of the residues B1 through B8 being Cys;
a is an integer between 3 to 25;
b is an integer between 0 to 2;
c is an integer between 5 to 50;
d is an integer between 2 to 35;
e is an integer between 2 to 15;
f is an integer between 0 to 2; and
g is an integer between 3 to 35.

6. The method according to any preceding paragraph, wherein at least one of the one or more hydrophobins has the general formula (III):

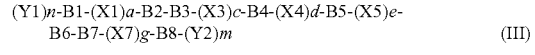

$(Y1)_n$-B1-$(X1)_a$-B2-B3-$(X3)_c$-B4-$(X4)_d$-B5-$(X5)_e$-B6-B7-$(X7)_g$-B8-$(Y2)_m$ (III)

wherein:
m and n are independently an integer between 0 to 20;
B1, B2, B3, B4, B5, B6, B7 and B8 are each independently amino acids selected from Cys, Leu, Ala, Pro, Ser, Thr, Met or Gly, at least 7 of the residues B1 through B8 being Cys;
a is an integer between 5 to 15;
c is an integer between 5 to 40;
d is an integer between 4 to 23;
e is an integer between 5 to 12; and
g is an integer between 6 to 21.

7. The method according to any preceding paragraph, wherein all 8 of the residues B1 through B8 are Cys.

8. The method according to any preceding paragraph, wherein at least one of the one or more hydrophobins is a hydrophobin fusion protein.

9. The method according to any preceding paragraph, wherein at least one of the one or more hydrophobins is obtained or obtainable from a filamentous fungus.

10. The method according to paragraph 9, wherein at least one of the one or more hydrophobins is obtained or obtainable from a fungus of genus selected from the group consisting of *Cladosporium, Ophistoma, Cryphonectria, Trichoderma, Gibberella, Neurospora, Maganaporthe, Hypocrea, Xanthoria, Emericella, Aspergillus, Paracoccioides, Metarhizium, Pleurotus, Coprinus, Dicotyonema, Flammulina, Schizophyllum, Agaricus, Pisolithus, Tricholoma, Pholioka, Talaromyces* and *Agrocybe*.

11. The method according to any preceding paragraph, wherein at least one of the one or more hydrophobins is generated in situ in the fermentation process.

12. The method according to any preceding paragraph, wherein the hydrophobin causes the equilibrium surface tension at a water/air interface to reduce to below 70 mN/m, below 50 mN/m or below 40 mN/m, or below 30 mN/m.

13. The method according to any preceding paragraph, wherein the hydrophobin causes the surface shear elasticity at a water/air interface to increase to 0.5-0.7 N/m or higher.

14. The method according to any preceding paragraph, wherein the hydrophobin causes at least 1 to 2 fold increase in stability of bubbles in the fermentation medium compared to the stability in the absence of said hydrophobin.

15. The method according to any preceding paragraph, wherein the hydrophobin causes at least a 10% increase in the number of bubbles in the fermentation medium compared to the number of bubbles in the absence of said hydrophobin.

16. The method according to any preceding paragraph, wherein said hydrophobin provides a decrease in an equilibrium surface tension of said fermentation medium below 50 mN/m.

17. The method according to any preceding paragraph, wherein said hydrophobin causes the surface shear elasticity of said fermentation medium to increase to 0.5-0.7 N/m or higher.

18. The method according to any preceding paragraph, wherein said hydrophobin causes the viscous modulus (G″s) of said fermentation medium to increase to 0.02-0.05 N/m.

19. The method according to any preceding paragraph, wherein at least one of the one or more hydrophobins is a Class II hydrophobin.

20. The method according to paragraph 19, wherein the hydrophobin is a Class II hydrophobin having the general formula (IV):

$(Y1)_n$-B1-$(X1)_a$-B2-B3-$(X3)_c$-B4-$(X4)_d$-B5-$(X5)_e$-B6-B7-$(X7)_g$-B8-$(Y2)_m$     (IV)

wherein:
m and n are independently an integer between 0 to 200;
B1, B2, B3, B4, B5, B6, B7 and B8 are each an amino acid independently selected from the group consisting of Cys, Leu, Ala, Ser, Thr, Met or Gly, at least 6 of the residues B1 through B8 being Cys;
  a is an integer between 6 to 12;
  c is an integer between 8 to 16;
  d is an integer between 2 to 20;
  e is an integer between 4 to 12; and
  g is an integer between 5 to 15.

21. The method according to paragraph 19 or paragraph 20, wherein the hydrophobin is a Class II hydrophobin having the general formula (V):

$(Y1)_n$-B1-$(X1)_a$-B2-B3-$(X3)_c$-B4-$(X4)_d$-B5-$(X5)_e$-B6-B7-$(X7)_g$-B8-$(Y2)_m$     (V)

wherein:
m and n are independently an integer between 0 to 10;
B1, B2, B3, B4, B5, B6, B7 and B8 are each an amino acid independently selected from the group consisting of Cys, Leu or Ser, at least 7 of the residues B1 through B8 being Cys;
  a is an integer between 7 to 11;
  c is 11;
  d is an integer between 4 to 18;
  e is an integer between 6 to 10; and
  g is an integer between 7 to 10.

22. The method according to any one of paragraphs 19 to 21, wherein all 8 of the residues B1 through B8 are Cys.

23. The method according to any one of paragraphs 19 to 22, wherein the group $(X3)_c$ comprises the sequence motif ZZXZ, wherein Z is an aliphatic amino acid; and X is any amino acid.

24. The method according to any preceding paragraph, wherein the hydrophobin is present in a concentration of 0.1-400 μM, or 5-125 μM, or 14-69 μM.

25. The method according to any preceding paragraph, wherein the hydrophobin is present in a concentration of 50-1000 mg/kg by weight of the total weight of the fermentation medium.

26. The method according to any preceding paragraph, wherein the hydrophobin is present in a concentration of 0.72-2900 mg/L, or 36-900 mg/L, or 100-500 mg/L.

27. The method according to any preceding paragraph, wherein the hydrophobin is present in a concentration of 100-500 mg/kg.

28. The method according to any preceding paragraph, wherein the hydrophobin is present in a concentration of 100 mg/kg.

29. The method according to any preceding paragraph, wherein the hydrophobin is present in a concentration of 250 mg/kg.

30. The method according to any preceding paragraph, wherein the hydrophobin is present in a concentration of 500 mg/kg.

31. A fermentation medium comprising a host cell and one or more hydrophobins, wherein an amount of at least one of said one or more hydrophobins in said fermentation medium is higher than an amount of hydrophobin produced by said host cell.

32. A fermentation medium comprising a host cell and one or more hydrophobins, wherein said host cell comprises either one or more nucleotide sequences or one or more expression vectors comprising a polynucleotide sequence encoding at least one of the one or more hydrophobins, and wherein said host is used in the recombinant production of said one or more hydrophobins and a product of interest that is different from said one or more hydrophobin.

33. The fermentation medium of paragraphs 31 or 32, wherein at least one of the one or more hydrophobins has the general formula (I):

$(Y1)_n$-B1-$(X1)_a$-B2-$(X2)_b$-B3-$(X3)_c$-B4-$(X4)_d$-B5-$(X5)_e$-B6-$(X6)_f$-B7-$(X7)_g$-B8-$(Y2)_m$     (I)

wherein:
m and n are independently an integer between 0 to 2000;
B1, B2, B3, B4, B5, B6, B7 and B8 are each an amino acid independently selected from the group consisting of Cys, Leu, Ala, Pro, Ser, Thr, Met or Gly, at least 6 of the residues B1 through B8 being Cys;

X1, X2, X3, X4, X5, X6, X7, Y1 and Y2 independently represent any amino acid;
- a is an integer between 1 to 50;
- b is an integer between 0 to 5;
- c is an integer between 1 to 100;
- d is an integer between 1 to 100;
- e is an integer between 1 to 50;
- f is an integer between 0 to 5; and
- g is an integer between 1 to 100.

34. The fermentation medium of any of paragraphs 31 or 33, wherein said host cell produces a product of interest than is not hydrophobin.

35. The fermentation medium of any of the paragraphs 31 or 33, wherein said host cell comprises either a nucleotide sequence or an expression vector and wherein said host used in the recombinant production of a product of interest that is different from a hydrophobin.

36. The fermentation medium of paragraphs 32, 34 or 35, wherein said product of interest is selected from the group consisting of proteins, alcohols, organic compounds, carbohydrates, or polymers.

37. The fermentation medium of paragraph 36, wherein the product of interest is a protein.

38. The fermentation medium of paragraph 37, wherein the protein is an enzyme.

39. The fermentation medium according to paragraphs 32, 34 or 35, wherein the product of interest is one or more alcohols such as n-butanol and ethanol, and acetic acid.

40. The fermentation medium according to paragraphs 32, 34 or 35, wherein the product of interest is one or more organic compounds such as isoprene or 1,3-propanediol.

41. The fermentation medium according to any preceding paragraph, wherein at least one of the one or more hydrophobins has a sequence of between 40 and 120 amino acids in length in the hydrophobin core.

42. The fermentation medium according to any preceding paragraph, wherein at least one of the one or more hydrophobins has the general formula (II):

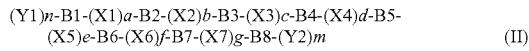
(Y1)$n$-B1-(X1)$a$-B2-(X2)$b$-B3-(X3)$c$-B4-(X4)$d$-B5-(X5)$e$-B6-(X6)$f$-B7-(X7)$g$-B8-(Y2)$m$   (II)

wherein:

m and n are independently an integer between 0 to 20;

B1, B2, B3, B4, B5, B6, B7 and B8 are each an amino acid independently selected from the group consisting of Cys, Leu, Ala, Pro, Ser, Thr, Met or Gly, at least 7 of the residues B1 through B8 being Cys;
- a is an integer between 3 to 25;
- b is an integer between 0 to 2;
- c is an integer between 5 to 50;
- d is an integer between 2 to 35;
- e is an integer between 2 to 15;
- f is an integer between 0 to 2; and
- g is an integer between 3 to 35.

43. The fermentation medium according to any preceding paragraph, wherein at least one of the one or more hydrophobins has the general formula (III):

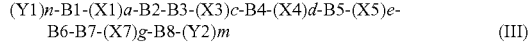
(Y1)$n$-B1-(X1)$a$-B2-B3-(X3)$c$-B4-(X4)$d$-B5-(X5)$e$-B6-B7-(X7)$g$-B8-(Y2)$m$   (III)

wherein:

m and n are independently an integer between 0 to 20;

B1, B2, B3, B4, B5, B6, B7 and B8 are each an amino acid independently selected from the group consisting of Cys, Leu, Ala, Pro, Ser, Thr, Met or Gly, at least 7 of the residues B1 through B8 being Cys;
- a is an integer between 5 to 15;
- c is an integer between 5 to 40;
- d is an integer between 4 to 23;
- e is an integer between 5 to 12; and
- g is an integer between 6 to 21.

44. The fermentation medium according to any preceding paragraph, wherein all 8 of the residues B1 through B8 are Cys.

45. The fermentation medium according to any preceding paragraph, wherein at least one of the one or more hydrophobins is a hydrophobin fusion protein.

46. The fermentation medium according to any preceding paragraph, wherein at least one of the one or more hydrophobins is obtained or obtainable from a filamentous fungus.

47. The fermentation medium according to paragraph 46, wherein at least one of the one or more hydrophobins is obtained or obtainable from a fungus of genus selected from the group consisting of *Cladosporium*, *Ophistoma*, *Cryphonectria*, *Trichoderma*, *Gibberella*, *Neurospora*, *Magaunaporthe*, *Hypocrea*, *Xanthoria*, *Emericella*, *Aspergillus*, *Paracoccioides*, *Metarhizium*, *Pleurotus*, *Coprinus*, *Dicotyonema*, *Flammulina*, *Schizophyllum*, *Agaricus*, *Pisolithus*, *Tricholoma*, *Pholioka*, *Talaromyces* and *Agrocybe*.

48. The fermentation medium according to any preceding paragraph, wherein at least of the one or more hydrophobins is generated in situ in the fermentation medium.

49. The fermentation medium according to any preceding paragraph, wherein the hydrophobin causes the equilibrium surface tension at a water/air interface to reduce to 70 mN/m, or below 50 mN/m, or below 40 mN/m, or below 30 mN/m.

50. The fermentation medium according to any preceding paragraph, wherein the hydrophobin causes the surface shear elasticity at a water/air interface to increase to 0.5-0.7 N/m or higher.

51 The fermentation medium according to any preceding paragraph, wherein the hydrophobin causes at least 1 to 2 fold increase in stability of bubbles in the fermentation medium compared to the stability in the absence of said hydrophobin.

52. The fermentation medium according to any preceding paragraph, wherein the hydrophobin causes at least a 10% increase in the number of bubbles in the fermentation medium compared to the number of bubbles in the absence of said hydrophobin.

53. The fermentation medium according to any preceding paragraph, wherein said hydrophobin provides a decrease in an equilibrium surface tension at said fermentation medium below 50 mN/m.

54. The fermentation medium according to any preceding paragraph, wherein said hydrophobin causes the surface shear elasticity at said fermentation medium to increase to 0.5-0.7 N/m or higher.

55. The fermentation medium according to any preceding paragraph, wherein said hydrophobin causes the viscous modulus (G"s) of said fermentation medium to increase to 0.02-0.05 N/m.

56. The fermentation medium according to any preceding paragraph, wherein at least one of the one or more hydrophobins is a Class II hydrophobin.

57. The fermentation medium according to paragraph 56, wherein the hydrophobin is a Class II hydrophobin having the general formula (IV):

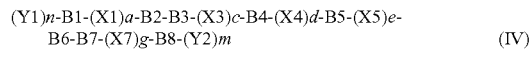
(Y1)$n$-B1-(X1)$a$-B2-B3-(X3)$c$-B4-(X4)$d$-B5-(X5)$e$-B6-B7-(X7)$g$-B8-(Y2)$m$   (IV)

wherein:

m and n are independently an integer between 0 to 200;

B1, B2, B3, B4, B5, B6, B7 and B8 are each an amino acid independently selected from the group consisting of Cys, Leu, Ala, Ser, Thr, Met or Gly, at least 6 of the residues B1 through B8 being Cys;

a is an integer between 6 to 12;

c is an integer between 8 to 16;

d is an integer between 2 to 20;

e is an integer between 4 to 12; and g is an integer between 5 to 15.

58. The fermentation medium according to paragraph 56 or paragraph 57, wherein the hydrophobin is a Class II hydrophobin having the general formula (V):

(Y1)$n$-B1-(X1)$a$-B2-B3-(X3)$c$-B4-(X4)$d$-B5-(X5)$e$-B6-B7-(X7)$g$-B8-(Y2)$m$  (V)

wherein:

m and n are independently is an integer between 0 to 10;

B1, B2, B3, B4, B5, B6, B7 and B8 are each an amino acid independently selected from the group consisting of Cys, Leu or Ser, at least 7 of the residues B1 through B8 being Cys;

a is an integer between 7 to 11;

c is 11;

d is an integer between 4 to 18;

e is an integer between 6 to 10; and g is an integer between 7 to 10.

59. The fermentation medium according to any one of paragraphs 56 to 58, wherein all 8 of the residues B1 through B8 are Cys.

60. The fermentation medium according to any one of paragraphs 56 to 59, wherein the group (X3)c comprises the sequence motif ZZXZ, wherein Z is an aliphatic amino acid; and X is any amino acid.

61. The fermentation medium according to any preceding paragraph, wherein the hydrophobin is present in a concentration of 0.1-400 µM, or 5-125 µM, or 14-69 µM.

62. The fermentation medium according to any preceding paragraph, wherein the hydrophobin is present in a concentration of 50-1000 mg/kg by weight of the total weight of the fermentation medium.

63. The fermentation medium according to any preceding paragraph, wherein the hydrophobin is present in a concentration of 0.72-2900 mg/L, or 36-900 mg/L, or 100-500 mg/L.

64. The fermentation medium according to any preceding paragraph, wherein the hydrophobin is present in a concentration of 100-500 mg/kg.

65. The fermentation medium according to any preceding paragraph, wherein the hydrophobin is present in a concentration of 100 mg/kg.

66. The fermentation medium according to any preceding paragraph, wherein the hydrophobin is present in a concentration of 250 mg/kg.

67. The fermentation medium according to any preceding paragraph, wherein the hydrophobin is present in a concentration of 500 mg/kg.

68. The method or fermentation medium of any of the preceding paragraphs, wherein said hydrophobin is selected from the groups consisting of HFBII (SEQ ID NO: 2), HFBI (SEQ ID NO: 4), SC3 (SEQ ID NO: 6), EAS (SEQ ID NO: 8) and TT1 (SEQ ID NO: 10), or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core to any thereof.

69. The method or fermentation medium of any of the preceding paragraphs, wherein said hydrophobin is "HFBII" (SEQ ID NO: 2), or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core thereof.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which:

FIGS. 3-12 show SEQ ID NOs 1-10, respectively.

DETAILED DESCRIPTION OF THE INVENTION

Figure 1:
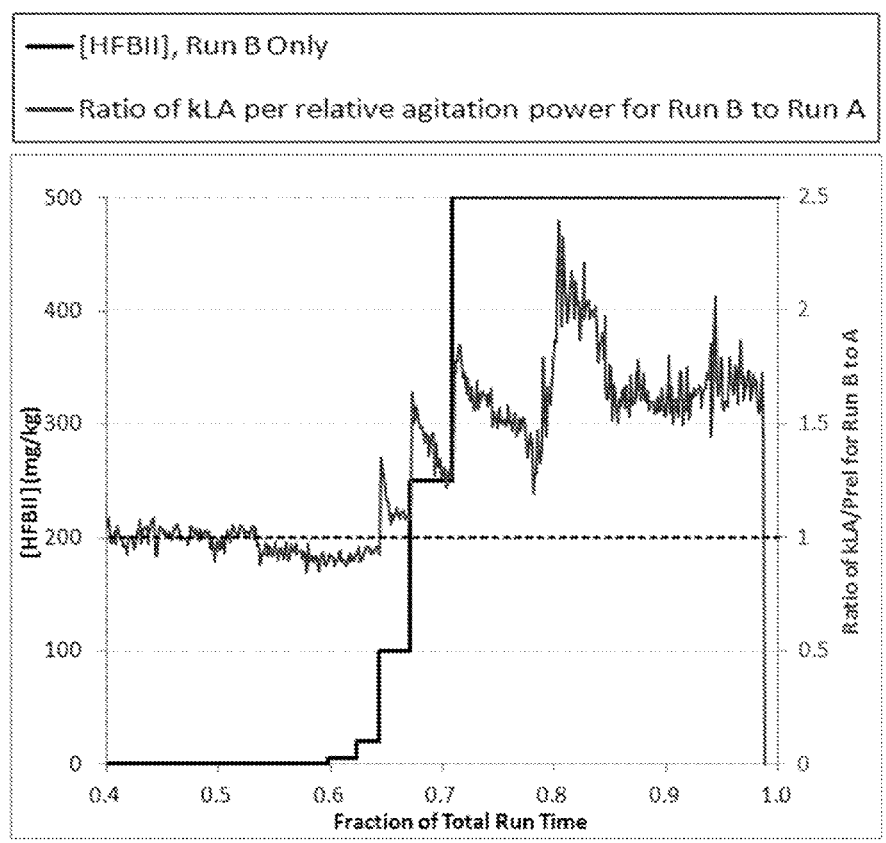
FIG. 1 shows the ratio of kLA per relative agitation power for Run B to Run A (unitless): Data for the first 40% of the run time are not shown because respiration rates during this period are very low and hence introduce excessive noise.

The present disclosure provides compositions, methods and apparatuses to increase gas transfer in aerobic fermentation processes. In some embodiments, the present disclosure provides compositions, methods and apparatuses to increase gas transfer in aerobic fermentation processes by addition of one or more hydrophobins. In some embodiments, the present disclosure provides compositions, methods and apparatuses for increasing oxygen transfer or transfer of other gases in aerobic submerged culture fermentation processes by addition of one or more hydrophobins.

INTRODUCTION

The ease of gas-liquid mass transfer can be quantitatively described by a volumetric mass transfer coefficient, kLA ($h^{-1}$). It can be written for any gas, but is most commonly written for oxygen:

$$k_L A = \frac{OTR}{C^*_{L,O2} - C_{L,O2}}$$

where OTR is the oxygen transfer rate (mmol $L^{-1}$ $h^{-1}$) and the denominator is the liquid phase concentration of oxygen at equilibrium minus the actual measured liquid phase concentration of oxygen, i.e. the thermodynamic driving force. Thus, kLA is the rate of oxygen transfer per unit of driving force.

Not intending to be bound by any theory, several factors influence kLA, notably: (i) factors that increase the diffusivity of oxygen in the liquid or gas phase will increase kLA, e.g. lower viscosity or higher temperature; (ii) factors that increase the gas-liquid interfacial surface area, e.g., agitation rate: a higher rate of agitation will tend to create smaller bubbles, increasing gas-liquid interfacial surface area for a given volume of gas holdup; (iii) increased air flow rate tends to increase kLA because it increases gas holdup volume, and thus gas-liquid interfacial surface area (above a certain critical level, however, an increase in air flow rate will be detrimental to kLA because it will cause flooding of the impellers and result in geysering); and (iv) antifoamers and defoamers tend to decrease kLA because they cause bubbles to coalesce more easily.

In some embodiments, the present disclosure provides compositions, methods and apparatuses for increasing the transfer of a gas (e.g. oxygen transfer) in aerobic submerged culture fermentation processes by addition of one or more hydrophobins. Thus, in some embodiments, the invention provides compositions, methods and apparatuses to improve the kLA in an aerobic fermentation processes by addition of one or more hydrophobins.

Hydrophobin

Hydrophobins are small, cysteine-rich amphiphilic proteins typically produced by filamentous fungi. Because of their amphiphilic nature, hydrophobins tend to spontaneously adsorb at air/water interfaces, where they form multimers or two-dimensional layers. Hydrophobins (e.g. HFBII), have a well-documented ability to stabilize foams, increase formation of small air bubbles in stirred solutions, dramatically slow disproportionation rate, and increase elasticity of air/water interfaces.

Without intending to be limited to any theory, hydrophobins' ability to improve the kLA of fermentation process, as described herein, is at least partly due to its ability to increase the formation of and stabilize small bubbles in liquid solutions. It is also possible that hydrophobin increases kLA by decreasing the air/liquid interfacial mass transfer resistance.

In this specification the term "hydrophobin" is defined as used to refer to a polypeptide capable of self-assembly at a hydrophilic/hydrophobic interface, and having the general formula (I):

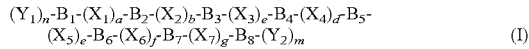
(I)

wherein: m and n are independently 0 to 2000; $B_1$, $B_2$, $B_3$, $B_4$, $B_5$, $B_6$, $B_7$ and $B_8$ are each amino acids independently selected from Cys, Leu, Ala, Pro, Ser, Thr, Met or Gly, at least 6 of the residues $B_1$ through $B_8$ being Cys; $X_1$, $X_2$, $X_3$, $X_4$, $X_5$, $X_6$, $X_7$, $Y_1$ and $Y_2$ independently represents any amino acid; a is an integer between 1 to 50; b is an integer between 0 to 5; c is an integer between 1 to 100; d is an integer between 1 to 100; e is an integer between 1 to 50; f is an integer between 0 to 5; and g is an integer between 1 to 100.

In some embodiments, the hydrophobin has a sequence of between 40 and 120 amino acids in the hydrophobin core. In some embodiments, the hydrophobin has a sequence of between 45 and 100 amino acids in the hydrophobin core. In some embodiments, the hydrophobin has a sequence of between 50 and 90, preferably 50 to 75, or 55 to 65 amino acids in the hydrophobin core. The term "the hydrophobin core" means the sequence beginning with the residue $B_1$ and terminating with the residue $B_8$.

In the formula (I), at least 6, or at least 7, or all 8 of the residues $B_1$ through $B_8$ are Cys.

In the formula (I), in some embodiments m is suitably an integer between 0 to 500, or an integer between 0 to 200, or an integer between 0 to 100, or an integer between 0 to 20, or an integer between 0 to 10, or an integer between 0 to 5, or 0.

In the formula (I), in some embodiments n is suitably an integer between 0 to 500, or an integer between 0 to 200, or an integer between 0 to 100, or an integer between 0 to 20, or an integer between 0 to 10, or an integer between 0 to 3.

In the formula (I), in some embodiments, is an integer between 3 to 25, or an integer between 5 to 15. In one embodiment, a is an integer between 5 to 9.

In the formula (I), in some embodiments, b is an integer between 0 to 2, or preferably 0.

In the formula (I), in some embodiments, c is an integer between 5 to 50, or an integer between 5 to 40. In some embodiments, c is an integer between 11 to 39.

In the formula (I), in some embodiments, d is an integer between 2 to 35, or an integer between 4 to 23. In some embodiments, d is an integer between 8 to 23.

In the formula (I), in some embodiments, e is an integer between 2 to 15, or an integer between 5 to 12. In some embodiments, e is an integer between 5 to 9.

In the formula (I), in some embodiments, f is an integer between 0 to 2, or 0.

In the formula (I), in some embodiments, g is an integer between 3 to 35, or 6 to 21. In one embodiment, g is an integer between 6 to 18.

In some embodiments, the hydrophobins used in the present invention have the general formula (II):

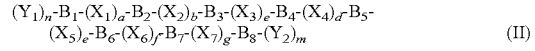
(II)

wherein: m and n are independently an integer between 0 to 20; $B_1$, $B_2$, $B_3$, $B_4$, $B_5$, $B_6$, $B_7$ and $B_8$ are each amino acids independently selected from Cys, Leu, Ala, Pro, Ser, Thr, Met or Gly, at least 7 of the residues $B_1$ through $B_8$ being Cys; a is an integer between 3 to 25; b is an integer between 0 to 2; c is an integer between 5 to 50; d is an integer between 2 to 35; e is an integer between 2 to 15; f is an integer between 0 to 2; and g is an integer between 3 to 35.

In the formula (II), at least 7, or all 8 of the residues $B_1$ through $B_8$ are Cys.

In some embodiments, the hydrophobins used in the present invention have the general formula (III):

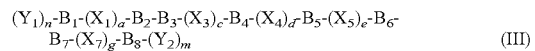
(III)

wherein: m and n are independently an integer between 0 to 20; $B_1$, $B_2$, $B_3$, $B_4$, $B_5$, $B_6$, $B_7$ and $B_8$ are each amino acids independently selected from Cys, Leu, Ala, Pro, Ser, Thr, Met or Gly, at least 7 of the residues $B_1$ through $B_8$ being Cys; a is an integer between 5 to 15; c is an integer between 5 to 40; d is an integer between 4 to 23; e is an integer between 5 to 12; and g is an integer between 6 to 21.

In the formula (III), at least 7, or 8 of the residues $B_1$ through $B_8$ are Cys.

In the formulae (I), (II) and (III), when 6 or 7 of the residues $B_1$ through $B_8$ are Cys, it is preferred that the residues $B_3$ through $B_7$ are Cys.

In the formulae (I), (II) and (III), when 7 of the residues $B_1$ through $B_8$ are Cys, in some embodiments: (a) $B_1$ and $B_3$ through $B_8$ are Cys and $B_2$ is other than Cys; (b) $B_1$ through $B_7$ are Cys and $B_8$ is other than Cys, (c) $B_1$ is other than Cys and $B_2$ through $B_8$ are Cys. When 7 of the residues $B_1$ through $B_8$ are Cys, it is preferred that the other residue is Ser, Pro or Leu. In some embodiments, $B_1$ and $B_3$ through $B_8$ are Cys and $B_2$ is Ser. In some embodiments, $B_1$ through $B_7$ are Cys and $B_8$ is Leu. In further embodiments, $B_1$ is Pro and $B_2$ through $B_8$ are Cys.

The cysteine residues of the hydrophobins used in the present invention may be present in reduced form or form disulfide (—S—S—) bridges with one another in any possible combination. In some embodiments, when all 8 of the residues $B_1$ through $B_8$ are Cys, disulfide bridges may be formed between one or more (preferably at least 2, more preferably at least 3, most preferably all 4) of the following pairs of cysteine residues: $B_1$ and $B_6$; $B_2$ and $B_5$; $B_3$ and $B_4$; $B_7$ and $B_8$. In some embodiments, when all 8 of the residues $B_1$ through $B_8$ are Cys, disulfide bridges may be formed between one or more (at least 2, or at least 3, or all 4) of the following pairs of cysteine residues: $B_1$ and $B_2$; $B_3$ and $B_4$; $B_5$ and $B_6$; $B_7$ and $B_8$.

Examples of specific hydrophobins useful in the present invention include those described and exemplified in the following publications: Linder et al., *FEMS Microbiology Rev.* 2005, 29, 877-896; Kubicek et al., *BMC Evolutionary Biology*, 2008, 8, 4; Sunde et al., *Micron*, 2008, 39, 773-784; Wessels, *Adv. Micr. Physiol.* 1997, 38, 1-45; Wosten, *Annu. Rev. Microbiol.* 2001, 55, 625-646; Hektor and Scholtmeijer, *Curr. Opin. Biotech.* 2005, 16, 434-439; Szilvay et al., *Biochemistry*, 2007, 46, 2345-2354; Kisko et al. *Langmuir*, 2009, 25, 1612-1619; Blijdenstein, *Soft Matter*, 2010, 6, 1799-1808; Wösten et al., *EMBO J.* 1994, 13, 5848-5854; Hakanpää et al., *J. Biol. Chem.*, 2004, 279, 534-539; Wang et al.; *Protein Sci.*, 2004, 13, 810-821; De Vocht et al., *Biophys. J.* 1998, 74, 2059-2068; Askolin et al., *Biomacromolecules* 2006, 7, 1295-1301; Cox et al.; *Langmuir*, 2007, 23, 7995-8002; Linder et al., *Biomacromolecules* 2001, 2, 511-517; Kallio et al. *J. Biol. Chem.*, 2007, 282, 28733-28739; Scholtmeijer et al., *Appl. Microbiol. Biotechnol.*, 2001, 56, 1-8; Lumsdon et al., *Colloids & Surfaces B: Biointerfaces*, 2005, 44, 172-178; Palomo et al., *Biomacromolecules* 2003, 4, 204-210; Kirkland and Keyhani, *J. Ind. Microbiol. Biotechnol.*, Jul. 17, 2010 (e-publication); Stübner et al., *Int. J. Food Microbiol.*, 30 Jun. 2010 (e-publication); Laaksonen et al. *Langmuir*, 2009, 25, 5185-5192; Kwan et al. *J. Mol. Biol.* 2008, 382, 708-720; Yu et al. *Microbiology*, 2008, 154, 1677-1685; Lahtinen et al. *Protein Expr. Purif.*, 2008, 59, 18-24; Szilvay et al., *FEBS Lett.*, 2007, 5811, 2721-2726; Hakanpää et al., *Acta Crystallogr. D. Biol. Crystallogr.* 2006, 62, 356-367; Scholtmeijer et al., *Appl. Environ. Microbiol.*, 2002, 68, 1367-1373; Yang et al, *BMC Bioinformatics*, 2006, 7 Supp. 4, S16; WO 01/57066; WO 01/57528; WO 2006/082253; WO 2006/103225; WO 2006/103230; WO 2007/014897; WO 2007/087967; WO 2007/087968; WO 2007/030966; WO 2008/019965; WO 2008/107439; WO 2008/110456; WO 2008/116715; WO 2008/120310; WO 2009/050000; US 2006/0228484; and EP 2042156A; the contents of which are incorporated herein by reference.

In some embodiments, the hydrophobin is a polypeptide selected from SEQ ID NOs: 2, 4, 6 8 or 10, or a polypeptide having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core to any of SEQ ID NOs: 2, 4, 6, 8, and 10, which retains the above-described self-assembly property of hydrophobins.

a. Sources of Hydrophobin

In one embodiment, the hydrophobin is obtained or obtainable from a microorganism. In some embodiments, the microorganism is a bacteria or a fungus, more preferably a fungus. In some embodiments, the hydrophobin is obtained or obtainable from a filamentous fungus.

In some embodiments, the hydrophobin is obtained or obtainable from fungi of the genera *Cladosporium* (particularly *C. fulvum* or *C. herbarum*), *Ophistoma* (particularly *O. ulmi*), *Cryphonectria* (particularly *C. parasitica*), *Trichoderma* (particularly *T. harzianum*, *T. longibrichiatum*, *T. asperellum*, *T. Koningiopsis*, *T. aggressivum*, *T. stromaticum* or *T. reesei*), *Gibberella* (particularly *G. moniliformis*), *Neurospora* (particularly *N. crassa*), *Maganaporthe* (particularly *M. grisea*), *Hypocrea* (particularly *H. jecorina, H. atroviridis, H. vixens* or *H. lixii*), *Xanthoria* (particularly *X. ectanoides* and *X. parietina*), *Emericella* (particularly *E. nidulans*), *Aspergillus* (particularly *A. fumigatus, A. oryzae*), *Paracoccioides* (particularly *P. brasiliensis*), *Metarhizium* (particularly *M. anisoplaie*), *Pleurotus* (particularly *P. ostreatus*), *Coprinus* (particularly *C. cinereas*), *Dicotyonema* (particularly *D. glabratum*), *Flammulina* (particularly *F. velutipes*), *Schizophyllum* (particularly *S. commune*), *Agaricus* (particularly *A. bisporus*), *Pisolithus* (particularly *P. tinctorius*), *Tricholoma* (particularly *T. terreum*), *Pholioka* (particularly *P. nameko*), *Talaromyces* (particularly *T. thermophiles*) or *Agrocybe* (particularly *A. aegerita*).

b. Class I and II Hydrophobins

In the art, hydrophobins are divided into Classes I and II. It is known in the art that hydrophobins of Classes I and II can be distinguished on a number of grounds, including solubility. As described herein, hydrophobins self-assemble at an interface (e.g., a water/air interface) into amphipathic interfacial films. The assembled amphipathic films of Class I hydrophobins are generally re-solubilised only in strong acids (typically those having a $pK_a$ of lower than 4, such as formic acid or trifluoroacetic acid), whereas those of Class II are soluble in a wider range of solvents.

In some embodiments, the hydrophobin is a Class II hydrophobin. In some embodiments, the hydrophobin is a Class I hydrophobin.

In some embodiments, the term "Class II hydrophobin" includes a hydrophobin (as defined and exemplified herein) having the above-described self-assembly property at a water/air interface, the assembled amphipathic films being capable of redissolving to a concentration of at least 0.1% (w/w) in an aqueous ethanol solution (60% v/v) at room temperature. In some embodiments, the term "Class I hydrophobin" includes a hydrophobin (as defined and exemplified herein) having the above-described self-assembly property but which does not have this specified redissolution property.

In some embodiments, the term "Class II hydrophobin" includes a hydrophobin (as defined and exemplified herein) having the above-described self-assembly property at a water/air interface and the assembled amphipathic films being capable of redissolving to a concentration of at least 0.1% (w/w) in an aqueous sodium dodecyl sulphate solution (2% w/w) at room temperature. In some embodiments, the term "Class I hydrophobin" includes a hydrophobin (as defined and exemplified herein) having the above-described self-assembly property but which does not have this specified redissolution property.

Hydrophobins of Classes I and II may also be distinguished by the hydrophobicity/hydrophilicity of a number of regions of the hydrophobin protein.

In some embodiments, the term "Class II hydrophobin" includes a hydrophobin (as defined and exemplified herein) having the above-described self-assembly property and in which the region between the residues $B_3$ and $B_4$, i.e. the moiety $(X_3)_c$, is predominantly hydrophobic. In some embodiments, the term "Class I hydrophobin" includes a hydrophobin (as defined and exemplified herein) having the above-described self-assembly property but in which the region between the residues $B_3$ and $B_4$, i.e. the group $(X_3)_c$, is predominantly hydrophilic.

In some embodiments, the term "Class II hydrophobin" includes a hydrophobin (as defined and exemplified herein) having the above-described self-assembly property and in which the region between the residues $B_7$ and $B_8$, i.e. the moiety $(X_7)_g$, is predominantly hydrophobic. In some embodiments, the term "Class I hydrophobin" includes a hydrophobin (as defined and exemplified herein) having the above-described self-assembly property but in which the region between the residues $B_7$ and $B_8$, i.e. the moiety $(X_7)_g$, is predominantly hydrophilic.

In some embodiments, the term "Class II hydrophobin" includes a hydrophobin (as defined and exemplified herein) having the above-described self-assembly property and in which the region between the residues $B_3$ and $B_4$, i.e. the moiety $(X_3)_c$, is predominantly hydrophobic. In some embodiments, the term "Class I hydrophobin" includes a hydrophobin (as defined and exemplified herein) having the above-described self-assembly property but in which the region between the residues $B_3$ and $B_4$, i.e. the group $(X_3)_c$, is predominantly hydrophilic.

In some embodiments, the term "Class II hydrophobin" includes a hydrophobin (as defined and exemplified herein) having the above-described self-assembly property and in which the region between the residues $B_7$ and $B_8$, i.e. the moiety $(X_7)_g$, is predominantly hydrophobic. In some embodiments, the term "Class I hydrophobin" includes a hydrophobin (as defined and exemplified herein) having the above-described self-assembly property but in which the region between the residues $B_7$ and $B_8$, i.e. the moiety $(X_7)_g$, is predominantly hydrophilic.

The relative hydrophobicity/hydrophilicity of the various regions of the hydrophobin protein can be established by comparing the hydropathy pattern of the hydrophobin using the method set out in Kyte and Doolittle, *J. Mol. Biol.*, 1982, 157, 105-132. A computer program can be used to progressively evaluate the hydrophilicity and hydrophobicity of a protein along its amino acid sequence. For this purpose, the method uses a hydropathy scale (based on a number of experimental observations derived from the literature) comparing the hydrophilic and hydrophobic properties of each of the 20 amino acid side-chains. The program uses a moving-segment approach that continuously determines the average hydropathy within a segment of predetermined length as it advances through the sequence. The consecutive scores are plotted from the amino to the carboxy terminus. At the same time, a midpoint line is printed that corresponds to the grand average of the hydropathy of the amino acid compositions found in most of the sequenced proteins. The method is further described for hydrophobins in Wessels, *Adv. Microbial Physiol.* 1997, 38, 1-45.

Class II hydrophobins may also be characterized by their conserved sequences.

In one embodiment, the Class II hydrophobins used in the present invention have the general formula (IV):

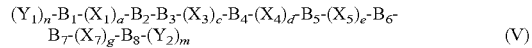
(IV)

wherein: m and n are independently an integer between 0 to 200; $B_1$, $B_2$, $B_3$, $B_4$, $B_5$, $B_6$, $B_7$ and $B_8$ are each amino acids independently selected from Cys, Leu, Ala, Ser, Thr, Met or Gly, at least 6 of the residues $B_1$ through $B_8$ being Cys; a is an integer between 6 to 12; c is an integer between 8 to 16; d is an integer between 2 to 20; e is an integer between 4 to 12; and g is an integer between 5 to 15.

In the formula (IV), in some embodiments, a is an integer between 7 to 11.

In the formula (IV), in some embodiments, c is an integer between 10 to 12. In some embodiments, c is 11.

In the formula (IV), in some embodiments, d is an integer between 4 to 18. In some embodiments, d is an integer between 4 to 16.

In the formula (IV), in some embodiments, e is an integer between 6 to 10. In some embodiments, e is an integer between 9 or 10.

In the formula (IV), in some embodiments, g is an integer between 6 to 12. In some embodiments, g is an integer between 7 to 10.

In some embodiments, the Class II hydrophobins used in the present invention have the general formula (V):

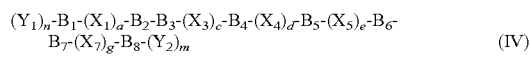
(V)

wherein: m and n are independently an integer between 0 to 10; $B_1$, $B_2$, $B_3$, $B_4$, $B_5$, $B_6$, $B_7$ and $B_8$ are each amino acids independently selected from Cys, Leu or Ser, at least 7 of the residues $B_1$ through $B_8$ being Cys; a is an integer between 7 to 11; c is 11; d is an integer between 4 to 18; e is an integer between 6 to 10; and g is an integer between 7 to 10.

In the formulae (IV) and (V), in some embodiments, at least 7 of the residues $B_1$ through $B_8$ are Cys, or all 8 of the residues $B_1$ through $B_8$ are Cys.

In the formulae (IV) and (V), in some embodiments, when 7 of the residues $B_1$ through $B_8$ are Cys, it is preferred that the residues $B_3$ through $B_7$ are Cys.

In the formulae (IV) and (V), in some embodiments, when 7 of the residues $B_1$ through $B_8$ are Cys, it is preferred that: (a) $B_1$ and $B_3$ through $B_8$ are Cys and $B_2$ is other than Cys; (b) $B_1$ through $B_7$ are Cys and $B_8$ is other than Cys, or (c) $B_1$ is other than Cys and $B_2$ through $B_8$ are Cys. In some embodiments, when 7 of the residues $B_1$ through $B_8$ are Cys, it is preferred that the other residue is Ser, Pro or Leu. In some embodiments, $B_1$ and $B_3$ through $B_8$ are Cys and $B_2$ is Ser. In some embodiments, $B_1$ through $B_7$ are Cys and $B_8$ is Leu. In some embodiments, $B_1$ is Pro and $B_2$ through $B_8$ are Cys.

In the formulae (IV) and (V), in some embodiments, the group $(X_3)_c$ comprises the sequence motif ZZXZ, wherein Z is an aliphatic amino acid; and X is any amino acid. The term "aliphatic amino acid" means an amino acid selected from the group consisting of glycine (G), alanine (A), leucine (L), isoleucine (I), valine (V) and proline (P).

In some embodiments, the group $(X_3)_c$ comprises the sequence motif selected from the group consisting of LLXV, ILXV, ILXL, VLXL and VLXV. In some embodiments, the group $(X_3)_c$ comprises the sequence motif VLXV.

In the formulae (IV) and (V), in some embodiments, the group $(X_3)_c$ comprises the sequence motif ZZXZZXZ, wherein Z is an aliphatic amino acid; and X is any amino acid. In some embodiments, the group $(X_3)_c$ comprises the sequence motif VLZVZXL, wherein Z is an aliphatic amino acid; and X is any amino acid.

In some embodiments, the hydrophobin is a polypeptide selected from SEQ ID NOs: 2, 4, 6, 8 or 10, or a polypeptide having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core to any of SEQ ID NOs: 2, 4, 6, 8 or 10. By "the hydrophobin core" it is meant the sequence beginning with the residue $B_1$ and terminating with the residue $B_8$.

In some embodiments, the hydrophobin is obtained or obtainable from fungi of the phylum Ascomycota. In some embodiments, the hydrophobin is obtained or obtainable from fungi of the genera *Cladosporium* (particularly *C. flavum*), *Ophistoma* (particularly *O. ulmi*), *Cryphonectria* (particularly *C. parasitica*), *Trichoderma* (particularly *T. harzianum, T. longibrichiatum, T. asperellum, T. Koningiopsis, T. aggressivum, T. stromaticum* or *T. reesei*), *Gibber-* ella (particularly *G. moniliformis*), *Neurospora* (particularly *N. crassa*), *Maganaporthe* (particularly *M. grisea*) or *Hypocrea* (particularly *H. jecorina, H. atroviridis, H. vixens* or *H. lixii*).

In some embodiments, the hydrophobin is obtained or obtainable from fungi of the genus *Trichoderma* (particularly *T. harzianum, T. longibrichiatum, T. asperellum, T. Koningiopsis, T. aggressivum, T. stromaticum* or *T. reesei*). In some embodiments, the hydrophobin is obtained or obtainable from fungi of the species *T. reesei*.

In some embodiments, the hydrophobin is selected from the group consisting of: (a) HFBII (SEQ ID NO: 2; obtainable from the fungus *Trichoderma reesei*); (b) HFBI (SEQ ID NO: 4; obtainable from the fungus *Trichoderma reesei*); (c) SC3 (SEQ ID NO: 6; obtainable from the fungus *Schizophyllum commune*); (d) EAS (SEQ ID NO: 8; obtainable from the fungus *Neurospora crassa*); and (e) TT1 (SEQ ID NO: 10; obtainable from the fungus *Talaromyces thermophilus*); or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core to any thereof.

In some embodiments, the hydrophobin is encoded by the polynucleotide selected from the group consisting of: (a) HFBII (SEQ ID NO: 1; obtainable from the fungus *Trichoderma reesei*); (b) HFBI (SEQ ID NO: 3; obtainable from the fungus *Trichoderma reesei*); (c) SC3 (SEQ ID NO: 5; obtainable from the fungus *Schizophyllum commune*); (d) EAS (SEQ ID NO: 7; obtainable from the fungus *Neurospora crassa*); and (e) TT1 (SEQ ID NO: 9; obtainable from the fungus *Talaromyces thermophilus*); or the protein encoded by a polynucleotide which is degenerate as a result of the genetic code to the polynucleotides defined in (a) to (e) above.

In some embodiments, the hydrophobin is "HFBII" (SEQ ID NO: 2; obtainable from *Trichoderma reesei*) or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core thereof.

In some embodiments, the hydrophobin may be present as an initial component of the composition. In another embodiment, the hydrophobin may be generated in situ in the composition (for example, by in situ hydrolysis of a hydrophobin fusion protein).

In some embodiments, the hydrophobin may be replaced wholly or partially with a chaplin. Chaplins are hydrophobin-like proteins which are also capable of self-assembly at a hydrophobic-hydrophilic interface, and are therefore functional equivalents to hydrophobins. Chaplins have been identified in filamentous fungi and bacteria such as Actinomycetes and *Streptomyces*. Unlike hydrophobins, they may have only two cysteine residues and may form only one disulphide bridge. Examples of chaplins are described in WO 01/74864, US 2010/0151525 and US 2010/0099844 and in Talbot, *Curr. Biol.* 2003, 13, R696-R698.

One property of the hydrophobins used in some embodiments of the present invention is the self-assembly property of the hydrophobins at a hydrophilic/hydrophobic interface.

Self-assembly can be detected by adsorbing the protein to polytetrafluoroethylene (TEFLON®) and using Circular Dichroism (CD) to establish the change in secondary structure exemplified by the occurrence of motifs in the CD spectrum corresponding to a newly formed α-helix) (De Vocht et al., *Biophys. J.* 1998, 74, 2059-2068). A full procedure for carrying out the CD spectral analysis can be found in Askolin et al. *Biomacromolecules,* 2006, 7, 1295-1301.

In some embodiments, the hydrophobins used in the present invention are characterized by their effect on the surface properties at an interface, e.g., at an air/water interface. The surface property may be surface tension (especially equilibrium surface tension) or surface shear rheology, particularly the surface shear elasticity (storage modulus), or the air/liquid interfacial mass resistance.

In some embodiments, the hydrophobin may cause increase formation of and stabilization of small bubbles in liquid solutions. In some embodiments, the formation of and stabilization of small bubbles is increased 5%, 10%, 15%, 25%, 30%, 40%, 45%, 50%, 60%, 70%, 80%, 90%, 100%, 200 or even 300% when compared to an equivalent process without hydrophobin. In some embodiments, the formation of and stabilization of small bubbles is increased 5%. In some embodiments, the formation of and stabilization of small bubbles is increased 10%. In some embodiments, the formation of and stabilization of small bubbles is increased 15%. In some embodiments, the formation of and stabilization of small bubbles is increased 25%.

In some embodiments, the hydrophobin may cause the equilibrium surface tension at a water/air interface to reduce to below 72 mN/m. In some embodiments, the hydrophobin may cause the equilibrium surface tension at a water/air interface to reduce to below 60 mN/m. In some embodiments, the hydrophobin may cause the equilibrium surface tension at a water/air interface to reduce to below 55 mN/m. In contrast, the surface tension of pure water is 72 mN/m at room temperature. In some embodiments, the hydrophobin may cause the equilibrium surface tension at a water/air interface to be between 15-55 mN/m. In some embodiments, the hydrophobin may cause the equilibrium surface tension at a water/air interface to be between 20-50 mN/m. In some embodiments, the hydrophobin may cause the equilibrium surface tension at a water/air interface to be between 28-43 mN/m. In some embodiments, the hydrophobin may cause the equilibrium surface tension at a water/air interface to be 50 mN/m. In some embodiments, such a reduction in the equilibrium surface tension at a water/air interface may be achieved using a hydrophobin concentration of between 0.1-400 μM, e.g., between 5-125 μM and 14-69 μM. In some embodiments such a reduction in the equilibrium surface tension at a water/air interface may be achieved at a temperature ranging from 0° C. to 50° C., especially room temperature. The change in equilibrium surface tension can be measured using a tensiometer following the method described in Cox et al., *Langmuir,* 2007, 23, 7995-8002.

In some embodiments, the hydrophobin may cause the surface shear elasticity (G'$_s$) at a water/air interface to increase to 0.5-0.7 mN/m, or higher. In some embodiments, the hydrophobin may cause the viscous modulus G"s at a water/air interface to increase to 0.02-0.05 N/m, or higher. In some embodiments, such a surface shear elasticity at a water/air interface may be achieved using a hydrophobin concentration of between 0.1-400 μM. In some embodiments, the hydrophobin is present in a concentration of 5-125 μM. In some embodiments, the hydrophobin is present in a concentration of 14-69 μM. In some embodiments, the hydrophobia is present in a concentration of 0.1-20% by weight of the total weight of the composition. In some embodiments, such a surface shear elasticity at a fermentation medium may be achieved at a temperature ranging from 0° C. to 50° C., especially room temperature. The change in equilibrium surface tension can be measured using a rheometer following the method described in Cox et al., *Langmuir*, 2007, 23, 7995-8002.

In some embodiments, the hydrophobins used in the present invention are biosurfactants. Biosurfactants are surface-active substances synthesized by living cells. Among other properties, they have the properties of reducing surface tension, stabilizing emulsions, promoting foaming and are generally non-toxic and biodegradable.

Examples of specific hydrophobins useful in the methods, compositions, kits and/or apparatuses of the present disclosure are listed in Table 1 below.

TABLE 1

| Organism | Gene, Protein name | NCBI accession code and version number |
|---|---|---|
| *Agaricus bisporus* | ABH3 | Y14602.1 |
| *Agaricus bisporus* | HYPB | Y15940.1 |
| *Aspergillus fumigatus* | HYP1/RODA | L25258.1, U06121.1 |
| *Aspergillus fumigatus* | RODB | AY057385.1 |
| *Aspergillus niger* | A_NIG1 | XM_001394993.1 |
| *Aspergillus oryzae* | HYPB | AB097448.1 |
| *Aspergillus oryzae* | ROLA | AB094496.1 |
| *Aspergillus terreus* | A_TER | XM_001213908.1 |
| *Cladosporium fulvum* | HCF-5 | AJ133703.1 |
| *Cladosporium fulvum* | HCF-6 | AJ251294.1 |
| *Cladosporium fulvum* | HCF-3 | AJ566186.1 |
| *Cladosporium fulvum* | HCF-1 | X98578.1 |
| *Cladosporium fulvum* | HCF-2 | AJ133700.1 |
| *Cladosporium fulvum* | HCF-4 | AJ566187.1 |
| *Cladosporium herbarum* | HCH-1 | AJ496190.1 |
| *Claviceps fusiformis* | CFTH1_I-III | AJ133774.1 |
| *Claviceps fusiformis* | CLF | CAB61236.1 |
| *Claviceps purpurea* | CLP | CAD10781.1 |
| *Claviceps purpurea* | CPPH1_I-V | AJ418045.1 |
| *Coprinus cinereus* | COH1 | Y10627.1 |
| *Coprinus cinereus* | COH2 | Y10628.1 |
| *Cryphonectria parasitica* | CRP | L09559.1 |
| *Dictyonema glabratum* | DGH3 | AJ320546.1 |
| *Dictyonema glabratum* | DGH2 | AJ320545.1 |
| *Dictyonema glabratum* | DGH1 | AJ320544.1 |
| *Emericella nidulans* | RODA | M61113.1 |
| *Emericella nidulans* | DEWA | U07935.1 |
| *Flammulina velutipes* | FVH1 | AB026720.1 |
| *Flammulina velutipes* | FvHYD1 | AB126686.1 |
| *Gibberella moniliformis* | HYD5, GIM | AY158024.1 |
| *Gibberella moniliformis* | HYD4 | AY155499.1 |
| *Gibberella moniliformis* | HYD1 | AY155496.1 |
| *Gibberella moniliformis* | HYD2 | AY155497.1 |
| *Gibberella moniliformis* | HYD3 | AY155498.1 |
| *Gibberella zeae* | GIZ, FG01831.1 | XP_382007.1 |
| *Lentinula edodes* | Le.HYD1 | AF217807.1 |
| *Lentinula edodes* | Le.HYD2 | AF217808.1 |
| *Magnaporthe grisea* | MGG4 | XM_364289.1 |
| *Magnaporthe grisea* | MGG2 | XM_001522792.1 |
| *Magnaporthe grisea* | MHP1, MGG1 | AF126872.1 |
| *Magnaporthe grisea* | MPG1 | L20685.2 |
| *Metarhizium anisopliae* | SSGA | M85281.1 |
| *Neurospora crassa* | NCU08192.1 | AABX01000408.1 |
| *Neurospora crassa* | EAS | AAB24462.1 |
| *Ophiostoma ulmi* | CU | U00963.1 |
| *Paracoccidioides brasilensis* | PbHYD2 | AY427793.1 |
| *Paracoccidioides brasilensis* | PbHYD1 | AF526275.1 |
| *Passalora fulva* | PF3 | CAC27408.1 |
| *Passalora fulva* | PF1 | CAC27407.1 |
| *Passalora fulva* | PF2 | CAB39312.1 |
| *Pholiota nameko* | PNH2 | AB079129.1 |
| *Pholiota nameko* | PNH1 | AB079128.1 |
| *Pisolithus tinctorius* | HYDPt-1 | U29605.1 |
| *Pisolithus tinctorius* | HYDPt-2 | U29606.1 |
| *Pisolithus tinctorius* | HYDPt-3 | AF097516.1 |
| *Pleurotus ostreatus* | POH2 | Y14657.1 |
| *Pleurotus ostreatus* | POH3 | Y16881.1 |

TABLE 1-continued

| Organism | Gene, Protein name | NCBI accession code and version number |
|---|---|---|
| *Pleurotus ostreatus* | VMH3 | AJ238148.1 |
| *Pleurotus ostreatus* | POH1 | Y14656.1 |
| *Pleurotus ostreatus* | FBHI | AJ004883.1 |
| *Schizophyllum commune* | SC4 | M32330.1 |
| *Schizophyllum commune* | SC1, 1G2 | X00788.1 |
| *Schizophyllum commune* | SC6 | AJ007504.1 |
| *Schizophyllum commune* | SC3 | AAA96324.1 |
| *Talaromyces thermophilus* | TT1 | |
| *Trichoderma harzianum* | QID3 | X71913.1 |
| *Trichoderma harzianum* | SRH1 | Y11841.1 |
| *Trichoderma reesei* | HFBII | P79073.1 |
| *Trichoderma reesei* | HFBI | P52754.1 |
| *Tricholoma terreum* | HYD1 | AY048578.1 |
| *Verticillium dahliae* | VED | AAY89101.1 |
| *Xanthoria ectaneoides* | XEH1 | AJ250793.1 |
| *Xanthoria parietina* | XPH1 | AJ250794.1 | c. Fusion Proteins

The hydrophobin of the present disclosure includes fusion proteins of a hydrophobin and another polypeptide as well as conjugates of hydrophobin and other molecules such as polysaccharides.

In some embodiments, the hydrophobin is a hydrophobin fusion protein. The term "fusion protein" includes a hydrophobin sequence (as defined and exemplified above) bonded to a further peptide sequence (described herein as "a fusion partner") which does not occur naturally in a hydrophobin.

In some embodiments, the fusion partner may be bonded to the amino terminus of the hydrophobin core, thereby forming the group $(Y_1)_m$. In some embodiments, m may range from 1 to 2000, or 2 to 1000, or 5 to 500, or 10 to 200, or 20 to 100.

In some embodiments, the fusion partner may be bonded to the carboxyl terminus of the hydrophobin core, thereby forming the group $(Y_2)_n$. In some embodiments, n may range from 1 to 2000, or 2 to 1000, or 5 to 500, or 10 to 200, or 20 to 100.

In some embodiments, fusion partners may be bonded to both the amino and carboxyl termini of the hydrophobin core. In some embodiments, the fusion partners may be the same or different, and may have amino acid sequences having the number of amino acids defined above by the stated values of m and n.

In some embodiments, the hydrophobin is not a fusion protein and m and n are 0.

Fermentation Processes

The methods, compositions, and apparatuses described herein can be used in any fermentation process that operates in a gas transfer regime (e.g. oxygen). The present disclosure provides compositions, methods and apparatuses for increasing gas transfer in aerobic fermentation processes. In some embodiments, the present disclosure provides compositions, methods and apparatuses to increase gas transfer in aerobic fermentation processes by addition of one or more hydrophobins. In some embodiments, the present disclosure provides compositions, methods and apparatuses to increase oxygen transfer or transfer of other gases in aerobic submerged culture fermentation processes by addition of one or more hydrophobins.

The fermentation process can be used to produce one or more products of interest such as proteins, alcohols, organic compounds, carbohydrates, or polymers. The fermentation process can be used to produce one or more proteins of interest such as enzymes. The fermentation process can be used to produce one or more alcohols such as n-butanol and ethanol, and acetic acid. The fermentation process can be used to produce one or more organic compounds such as isoprene or 1,3-propanediol. The fermentation process can be used to produce one or more antibiotics, chemicals, biochemicals, or other biologically derived products.

In various embodiments, the fermentation is carried out using a culture of one or more strains of a prokaryotic (for example bacterial), fungal, yeast or plant.

Examples of suitable bacterial species are gram positive or gram negative bacterial species. Examples of gram-positive bacteria species, include but are not limited to, *Bacillus* cells such as *Bacillus subtilis* cells or *Streptomyces* cells such as *Streptomyces lividans, Streptomyces coelicolor*, and *Streptomyces griseus* cells. Examples of gram-negative bacterial species, include but are not limited to *Escherichia* species such as *Escherichia coli* or *Pantoea* species such as *Pantoea citrea*.

Fermentation can be carried out using a fungus—such as a filamentous fungus. Examples of suitable such fungus include any member belonging to the genera *Fusarium, Thermomyces, Acremonium, Aspergillus, Penicillium, Mucor, Neurospora, Trichoderma* and the like. In one embodiment, the fermentation is carried out in *Trichoderma*, preferably *T. reesei*. The fermentation can be carried out using in *Aspergillus*, such as *Aspergillus niger*.

Depending on the nature of the product of interest, eukaryotic cells such as yeasts or other fungi may be preferred. A suitable yeast can be selected from the biotechnologically relevant yeasts species such as, but not limited to, yeast species selected from *Pichia* spp., *Hansenula* spp., *Kluyveromyces, Yarrowinia* spp., *Saccharomyces* spp., including *S. cerevisiae*, or *Schizosaccharomyce* spp., including *Schizosaccharomyce pombe*.

The fermentation can be carried out using plant. A review of the general techniques may be found in articles by Potrykus (Annu Rev Plant Physiol Plant Mol Biol (1991) 42:205-225) and Christou (Agro-Food-Industry Hi-Tech March/April 1994 17-27), or in WO 01/16308. A transgenic plant may produce enhanced levels of phytosterol esters and phytostanol esters, for example.

The medium used for the fermentation process may be any conventional medium suitable for growing the fermentation cell in question and obtaining expression of the desired product. Thus, the cells may be cultured under conditions conducive to the production of the desired product and which facilitate recovery of the product from the cells and/or culture medium. The product produced by a cell may be displayed on the surface of the cell. The product of interest may be secreted from the host cells and may conveniently be recovered from the culture medium using well-known procedures.

It will be appreciated that the fermentation should desirably be carried out under appropriate conditions for the desired fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations, and maximum product concentrations to avoid product inhibition. The optimum reaction conditions will depend partly on the particular micro-organism used.

Methods

In some embodiments, the present invention provides methods to increase gas transfer in aerobic fermentation processes. In some embodiments, the present disclosure provides methods to increase gas transfer in aerobic fermentation processes by addition of one or more hydrophobins. In some embodiments, the present methods to increase oxygen transfer or transfer of other gases in aerobic submerged culture fermentation processes by addition of one or more hydrophobins. In some embodiments, the present invention provides methods for stabilizing or increasing the number of bubbles in a fermentation medium using one or more hydrophobins.

In some embodiments, the methods of the invention comprise adding one or more hydrophobins to fermentation media to stabilize and/or increase bubbles and/or increase gas (e.g. oxygen) transfer in a fermentation medium. In some embodiments, the one or more hydrophobins are added to the fermentation medium in an amount sufficient to stabilize and/or increase bubbles and/or increase gas (e.g. oxygen) transfer in a fermentation medium. In some embodiments, a organism capable of producing hydrophobin is added to the fermentation medium.

In some embodiments, the methods of the invention comprise producing in situ during the fermentation process one or more hydrophobins in an amount sufficient to stabilize and/or increase bubbles and/or increase gas (e.g. oxygen) transfer in a fermentation medium. In some embodiments, a organism capable of producing hydrophobin is added to the fermentation medium. In some embodiments, a host cell that produces a product of interest, also produces hydrophobin into the fermentation medium.

In some embodiments, the hydrophobin concentration is suitably between 0.1 µM-1 M. In some embodiments, the hydrophobin concentration is between 0.1-400 µM. In some embodiments, the hydrophobin concentration is between 14-69 µM. In some embodiments, the hydrophobin concentration is between 0.5 µM-0.5 M. In some embodiments, the hydrophobin concentration is between 0.1 mM-200 mM. In some embodiments, the hydrophobin concentration is between 0.1 mM-100 mM. In some embodiments, the hydrophobin concentration is between 0.1 mM-100 mM. In some embodiments, the hydrophobin concentration is between 0.1 mM-50 mM. In some embodiments, the hydrophobin concentration is between 0.1 mM-20 mM. In some embodiments, the hydrophobin concentration is between 0.1 mM-10 mM. In some embodiments, the hydrophobin concentration is between 0.1 mM-5 mM. In some embodiments, the hydrophobin concentration is between 0.1 mM-1 mM. In some embodiments, the hydrophobin is present in a concentration of 0.1 µM-50 mM. In some embodiments, the hydrophobin is present in a concentration of 0.1-20% by weight of the total weight of the composition.

In some embodiments, the hydrophobin concentration is between suitably 50-1000 mg/kg. In some embodiments, the hydrophobin concentration is between 100-500 mg/kg. In some embodiments, the hydrophobin concentration is between 500-1000 mg/kg. In some embodiments, the hydrophobin concentration is between 500-1000 mg/kg. In some embodiments, the hydrophobin concentration is 100 mg/kg. In some embodiments, the hydrophobin concentration is between 250 mg/kg. In some embodiments, the hydrophobin concentration is between 500 mg/kg.

In some embodiments, the hydrophobin concentration is between suitably 0.5-2900 mg/L. In some embodiments, the hydrophobin concentration is between 0.72-2900 mg/L. In some embodiments, the hydrophobin concentration is between 36-900 mg/L. In some embodiments, the hydrophobin concentration is between 100-500 mg/L.

In some embodiments, the one or more hydrophobins is added to the fermentation medium at a concentration that is based on the critical aggregation concentration (CAC) of the one or more hydrophobins. The term "critical aggregation concentration" or "CAC" is the concentration above which the hydrophobins or other surfactants aggregate or form regular shaped structures, such as micelles, nanotubes or nanovesicles. The CAC of surfactants can be determined experimentally using known dynamic light scattering methods. A minimal amount of sample can be used in this method. Each CAC determination takes a few hours, therefore it is possible to determine the CAC for a large number of peptide detergents in a few weeks. It is known that the lower the CAC, the more hydrophobic the detergents and the stronger the aggregation in water.

In some embodiments, the one or more hydrophobins are added to the fermentation medium at a concentration from about 1 times the CAC of the one or more hydrophobins (1×CAC) to a concentration that is about 30 times the CAC of the one or more hydrophobins (30×CAC). In some embodiments, the one or more hydrophobins are added to the fermentation medium at a concentration which is at least 1.5 times the CAC of the one or more hydrophobins (1.5×CAC). In some embodiments, the one or more hydrophobins are added at a concentration that is at least 2 times the CAC of the one or more hydrophobins (2×CAC). In some embodiments, the one or more hydrophobins are added at a concentration that is at least 5 times the CAC of the one or more hydrophobins (5×CAC). In some embodiments, the one or more hydrophobins are added at a concentration that is at least 10 times the CAC of the one or more hydrophobins (10×CAC). In some embodiments, the one or more hydrophobins are added at a concentration that is at least 12 times the CAC of the one or more hydrophobins (12×CAC). In some embodiments, the one or more hydrophobins are added at a concentration that is at least 15 times the CAC of the one or more hydrophobins (15×CAC). In some embodiments, the one or more hydrophobins are added at a concentration that is at least 20 times the CAC of the one or more hydrophobins (20×CAC).

In some embodiments, a surfactant peptide and/or a non-peptide surfactant can be added to the fermentation medium. A surfactant is a compound that is amphiphilic or that contains both hydrophobic groups (their "tails") and hydrophilic groups (their "heads"). Surfactants are soluble in both organic solvents and water. There are generally two types of surfactants, ionic and non-ionic surfactants. Ionic surfactants are surfactants that have a net charge at their heads. Non-ionic surfactants are surfactants that have no net charge at their heads. Examples of non-peptide surfactants include, but are not limited to polyoxyalkylene sorbitan fatty acid esters, sorbitan fatty acid esters, alkylene glycol fatty acid esters, polyoxyalkylene fatty acid esters, fatty acid esters, polyoxyalkylene fatty acid ethers, $C_{16}C_{24}$ fatty acids, fatty acid mono-, di- or poly-glycerides, polyoxyalkylene alkyl phenols, alkyl phenyl ethers, polyoxyethylene polyoxypropylene block copolymers, fatty amine oxides, fatty acid alkanolamides, alkyl cellulose, carboxyalkyl cellulose and polyoxyalkylene castor oil derivatives. Ionic surfactants include, but are not limited to, alkyl sulfates, olefin sulfates, ether sulfates, monoglyceride sulfates, alkyl sulfonates, aryl sulfonates, olefin sulfonates, alkyl sulfosuccinates, aryl sulfosuccinates, including sodium lauryl sulfate, dioctyl sodium sulfosuccinate and dioctyl sodium sulfonate), benzalkonium salts, polyoxyalkylene alkylamines, alkylamines, alkanolamine fatty acid esters, quaternary ammonium fatty acid esters, dialkyl ammonium salts, alkyl pyridinium salts including stearylamine and triethanolamine oleate, benzethonium chloride. Non-limiting examples of non-peptide surfactant are lauryldimethyamine oxide (LDAO), n-dodecyldimethyamine N-oxide (NDAO), Octyldimethyamine N-oxide (ODAO), undecyldimethyamine N-oxide (UDAO), Octyl-.beta.-D-glucose (beta-OG), Decyl-beta-D-glucose (beta-DG), Nonyl-beta-D-glucose (beta-NG), Dodecyl-beta-D-maltoside (DDM), Octyanoylsucrose (OS), Octyl-beta-D-galactoside (beta-OGal) and Dodecyl phosphocholine (DPC). In some embodiments, the non-peptide surfactant used in the method of the invention is a non-ionic surfactant. In a further embodiment, the non-ionic surfactant is selected from the group consisting of n-dodecyl-B-D-maltoside and octyl-D-glucoside. In some embodiments, the non-peptide surfactant is added in an amount between about 2 and about 200 times the CAC of the non-peptide surfactant.

In some embodiments, addition of one or more hydrophobins provides at least about a 1 to 2-fold increase in stability and/or number of bubbles in fermentation medium compared to the stability and/or number of bubbles in the absence of the one or more hydrophobins. In another embodiment, addition of one or more hydrophobins provides at least about 1.5, at least about 1.7, at least about 2.0, at least about 2.2, at least about 2.3 or at least about 2.5-fold increase in stability and/or number of bubbles in fermentation medium compared to the stability and/or number of bubbles in the absence of the one or more hydrophobins.

In some embodiments, addition of one or more hydrophobins provides a decrease in the equilibrium surface tension at fermentation medium below 72 mN/m. In some embodiments, the hydrophobin may cause the equilibrium surface tension at a water/air interface to reduce to below 60 mN/m. In some embodiments, the hydrophobin may cause the equilibrium surface tension at a water/air interface to reduce to below 55 mN/m. In some embodiments, the hydrophobin may cause the equilibrium surface tension at a water/air interface to be between 15-55 mN/m. In some embodiments, the hydrophobin may cause the equilibrium surface tension at a water/air interface to be between 20-50 mN/m. In some embodiments, the hydrophobin may cause the equilibrium surface tension at a water/air interface to be between 28-43 mN/m. In some embodiments, the hydrophobin may cause the equilibrium surface tension at a water/air interface to be 50 mN/m. In some embodiments, such a reduction in the equilibrium surface tension at a fermentation medium may be achieved using one or more hydrophobins at a concentration of between 0.1-400 μM, e.g., between 5-125 μM and 14-69 μM. In some embodiments, the hydrophobin is present in a concentration of 0.1-20% by weight of the total weight of the composition. In some embodiments, such a reduction in the equilibrium surface tension at a fermentation medium may be achieved using one or more hydrophobins at a concentration of between 100-500 mg/kg. In some embodiments, such a reduction in the equilibrium surface tension at a fermentation medium may be achieved using one or more hydrophobins at a concentration of between 100-500 mg/L.

In some embodiments, addition of one or more hydrophobins causes the surface shear elasticity ($G'_s$) at a water/air interface to increase to 0.5-0.7 mN/m, or higher. In some embodiments, the hydrophobin may cause the viscous modulus G"s at a water/air interface to increase to 0.02-0.05 N/m, or higher. In some embodiments, such a surface shear elasticity at a water/air interface may be achieved using a hydrophobin concentration of between 0.1-400 μM. In some embodiments, the hydrophobin is present in a concentration of 5-125 µM. In some embodiments, the hydrophobin is present in a concentration of 14-69 µM. In some embodiments, the hydrophobin is present in a concentration of 0.1-20% by weight of the total weight of the composition. In some embodiments, the hydrophobin is present in a concentration of 0.1-20% by weight of the total weight of the composition. In some embodiments, such surface shear elasticity at a fermentation medium may be achieved using one or more hydrophobins at a concentration of between 100-500 mg/kg. In some embodiments, such surface shear elasticity at a fermentation medium may be achieved using one or more hydrophobins at a concentration of between 100-500 mg/L.

Host Cell

The term "host cell"—in relation to the present invention includes any cell that comprises either a nucleotide sequence or an expression vector as described herein and which is used in the recombinant production of one or more hydrophobins having the specific properties as defined herein or another product of interest such as a protein of interest.

A further embodiment of the present invention provides host cells transformed or transfected with a nucleotide sequence that expresses the protein(s) of the present invention. The cells will be chosen to be compatible with the said vector and may for example be prokaryotic (for example bacterial), fungal, yeast or plant cells. Preferably, the host cells are not human cells.

Examples of suitable bacterial host organisms are gram positive or gram negative bacterial species.

Depending on the nature of the nucleotide sequence encoding the hydrophobin of the present invention or another product of interest, and/or the desirability for further processing of the expressed protein, eukaryotic hosts such as yeasts or other fungi may be preferred. However, some proteins are either poorly secreted from the yeast cell, or in some cases are not processed properly (e.g., hyper-glycosylation in yeast).

The use of suitable host cells—such as yeast, fungal and plant host cells—may provide for post-translational modifications (e.g., myristoylation, glycosylation, truncation, lipidation and tyrosine, serine or threonine phosphorylation, or N-terminal acetylation as may be needed to confer optimal biological activity on recombinant expression products of the present invention.

The host cell may be a protease deficient or protease minus strain.

The genotype of the host cell may be modified to improve expression.

Examples of host cell modifications include protease deficiency, supplementation of rare tRNAs, and modification of the reductive potential in the cytoplasm to enhance disulphide bond formation.

For example, the host cell *E. coli* may overexpress rare tRNAs to improve expression of heterologous proteins as exemplified/described in Kane (*Curr Opin Biotechnol* (1995), 6, 494-500 "Effects of rare codon clusters on high-level expression of heterologous proteins in *E. coli*"). The host cell may be deficient in a number of reducing enzymes thus favoring formation of stable disulphide bonds as exemplified/described in Bessette (*Proc Natl Acad Sci USA* (1999), 96, 13703-13708 "Efficient folding of proteins with multiple disulphide bonds in the *Escherichia coli* cytoplasm").

Isolated

In one aspect, the polypeptide(s) for use in the present invention may be in an isolated form. The terms "polypeptide", "protein", "peptide" and "amino acid sequence" are used herein interchangeably.

The term "isolated" means that the sequence or protein is at least substantially free from at least one other component with which the sequence or protein is naturally associated in nature and as found in nature.

Purified

In one aspect, the polypeptide(s) for use in the present invention may be used in a purified form.

The term "purified" means that the sequence is in a relatively pure state—e.g., at least about 51% pure, or at least about 75%, or at least about 80%, or at least about 90% pure, or at least about 95% pure or at least about 98% pure.

Cloning a Nucleotide Sequence Encoding a Polypeptide According to the Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labeled oligonucleotide probes may be synthesized and used to identify polypeptide-encoding clones from the genomic library prepared from the organism. Alternatively, a labeled oligonucleotide probe containing sequences homologous to another known polypeptide gene could be used to identify polypeptide-encoding clones. In the latter case, hybridization and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g., the phosphoroamidite method described by Beucage S. L. et al. (1981) Tetrahedron Letters 22, 1859-1869, or the method described by Matthes et al. (1984) EMBO J. 3, 801-805. In the phosphoroamidite method, oligonucleotides are synthesized, e.g., in an automatic DNA synthesizer, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al. (Science (1988) 239, 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In some embodiments, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment.

However, the amino acid sequence encompassed by scope the present invention can be isolated and/or purified post expression of a nucleotide sequence in its native organism. In some embodiments, however, the amino acid sequence encompassed by scope of the present invention may be expressed by a nucleotide sequence in its native organism but wherein the nucleotide sequence is not under the control of the promoter with which it is naturally associated within that organism.

In some embodiments, the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e., recombinant DNA). However, in an alternative embodiment of the invention, the nucleotide sequence could be synthesized, in whole or in part, using chemical methods well known in the art (see Caruthers M H et al. (1980) Nuc Acids Res Symp Ser 215-23 and Horn T et al. (1980) Nuc Acids Res Symp Ser 225-232).

Molecular Evolution

Once a polypeptide-encoding nucleotide sequence has been isolated, or a putative polypeptide-encoding nucleotide sequence has been identified, it may be desirable to modify the selected nucleotide sequence, for example it may be desirable to mutate the sequence in order to prepare a polypeptide in accordance with the present invention.

Mutations may be introduced using synthetic oligonucleotides. These oligonucleotides contain nucleotide sequences flanking the desired mutation sites.

A suitable method is disclosed in Morinaga et al. (Biotechnology (1984) 2, 646-649). Another method of introducing mutations into polypeptide-encoding nucleotide sequences is described in Nelson and Long (Analytical Biochemistry (1989), 180, 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimizing PCR based mutagenesis, which can also be combined with the use of mutagenic DNA analogues such as those described in EP 0 866 796. Error prone PCR technologies are suitable for the production of variants of polypeptides with preferred characteristics.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of polypeptides with preferred characteristics. Suitable methods for performing 'shuffling' can be found in EP 0 752 008, EP 1 138 763, EP 1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo-mediated recombination methods (see, e.g., WO 00/58517, U.S. Pat. No. 6,344,328, U.S. Pat. No. 6,361,974), for example, molecular evolution can be performed where the variant produced retains very low homology to known proteins. Such variants thereby obtained may have significant structural analogy to known proteins, but have very low amino acid sequence homology.

As a non-limiting example, In addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the polypeptides of the present invention which have preferred characteristics without any prior knowledge of protein structure or function, and allows the production of non-predictable but beneficial mutations or variants. There are numerous examples of the application of molecular evolution in the art for the optimization or alteration of protein activity, such examples include, but are not limited to one or more of the following: optimized expression and/or activity in a host cell or in vitro, increased or decreased enzymatic activity, altered substrate and/or product specificity, increased or decreased structural stability, altered activity/specificity in preferred environmental conditions, e.g., temperature, pH, substrate.

As will be apparent to a person skilled in the art, using molecular evolution tools a polypeptide may be altered to improve the functionality of the polypeptide Alternatively, the variant polypeptide may have increased thermostability.

Amino Acid Sequences

The present invention also encompasses the use of amino acid sequences encoded by a nucleotide sequence which encodes a polypeptide for use in any one of the methods and/or uses of the present invention.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 μg of the freeze-dried material may be dissolved in 50 μl of a mixture of 8 M urea and 0.4 M ammonium hydrogen carbonate, pH 8.4. The dissolved protein may be denatured and reduced for 15 minutes at 50° C. following overlay with nitrogen and addition of 5 μl of 45 mM dithiothreitol. After cooling to room temperature, 5 μl of 100 mM iodoacetamide may be added for the cysteine residues to be derivatized for 15 minutes at room temperature in the dark under nitrogen. 135 μl of water and 5 μg of endoproteinase Lys-C in 5 μl of water may be added to the above reaction mixture and the digestion may be carried out at 37° C. under nitrogen for 24 hours. The resulting peptides may be separated by reverse phase HPLC on a VYDAC C18 column (0.46×15 cm; 10 μm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Life Technologies, California, USA).

Sequence Identity or Sequence Homology

Here, the term "homologue" means an entity having a certain homology with the subject amino acid sequences and the subject nucleotide sequences. Here, the term "homology" can be equated with "identity".

In some embodiments, the homologous amino acid sequence and/or nucleotide sequence provide and/or encode a polypeptide which retains the desire characteristic(s) and/or enhances the desire characteristic(s) of the polypeptide.

In the present context, a homologous sequence is taken to include an amino acid sequence which may be at least 50%, 55%, 60%, 70%, 71%, 72%, 73%, 74%, 75%, 80%, 85%, 90%, 91%, 92%, 93%, 94%, 95%, 96%, 97%, 98%, or 99% identical, preferably at least 95%, 96%, 97%, 98%, or 99% identical to the subject sequence. Typically, the homologues will comprise the same active sites etc. as the subject amino acid sequence. Although homology can also be considered in terms of similarity (i.e., amino acid residues having similar chemical properties/functions), in the context of the present invention it is preferred to express homology in terms of sequence identity.

In the present context, a homologous sequence is taken to include a nucleotide sequence which may be at least 75, 85 or 90%, 91%, 92%, 93%, 94%, 95%, 96%, 97%, 98%, or 99% identical, preferably at least 95%, 96%, 97%, 98%, or 99% identical to a nucleotide sequence encoding a polypeptide of the present invention (the subject sequence). In some embodiments, the homologues will comprise the same sequences that code for the active sites as the subject sequence. Although homology can also be considered in terms of similarity (e.g., amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e., one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximize local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimized alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of other software that can perform sequence comparisons include, but are not limited to, the BLAST package (see Ausubel et al. 1999 Short Protocols in Molecular Biology, $4^{th}$ Ed—Chapter 18), and FASTA (Altschul et al. 1990 *J. Mol. Biol.* 403-410). Both BLAST and FASTA are available for offline and online searching (see Ausubel et al. 1999, pages 7-58 to 7-60). However, for some applications, it is preferred to use the Vector NTI program. A new tool, called BLAST 2 Sequences is also available for comparing protein and nucleotide sequence (see *FEMS Microbiol Lett* 1999 174: 247-50; *FEMS Microbiol Lett* 1999 177: 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI ADVANCE™ 10 package.

Alternatively, percentage homologies may be calculated using the multiple alignment feature in Vector NTI ADVANCE™ 10 (Invitrogen Corp.), based on an algorithm, analogous to CLUSTAL (Higgins D G & Sharp P M (1988), *Gene* 73, 237-244).

Once the software has produced an optimal alignment, it is possible to calculate % homology, preferably % sequence identity. The software typically does this as part of the sequence comparison and generates a numerical result.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

Should Gap Penalties be used when determining sequence identity, then preferably the default parameters for the program are used for pairwise alignment. For example, the following parameters are the current default parameters for pairwise alignment for BLAST 2:

| FOR BLAST2 | DNA | PROTEIN |
|---|---|---|
| EXPECT THRESHOLD | 10 | 10 |
| WORD SIZE | 11 | 3 |
| SCORING PARAMETERS | | |
| Match/Mismatch Scores | 2, −3 | n/a |
| Matrix | n/a | BLOSUM62 |
| Gap Costs | Existence: 5 | Existence: 11 |
| | Extension: 2 | Extension: 1 |

In some embodiments, the sequence identity for the nucleotide sequences and/or amino acid sequences may be determined using BLAST2 (blastn) with the scoring parameters set as defined above.

In some embodiments, the degree of identity is based on the number of sequence elements which are the same. The degree of identity in accordance with the present invention for amino acid sequences may be suitably determined by means of computer programs known in the art such as Vector NTI ADVANCE™ 11 (Invitrogen Corp.). For pairwise alignment the scoring parameters used are preferably BLOSUM62 with Gap existence penalty of 11 and Gap extension penalty of 1.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids, preferably over at least 100 contiguous amino acids.

Suitably, the degree of identity with regard to an amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar- uncharged | C S T M |
| | | N Q |
| | Polar- charged | D E |
| | | K R |
| AROMATIC | | H F W Y |

The present invention also encompasses homologous substitution (substitution and replacement are both used herein to mean the interchange of an existing amino acid residue, with an alternative residue) that may occur, e.g., like-for-like substitution such as basic for basic, acidic for acidic, polar for polar etc. Non-homologous substitution may also occur, e.g., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine.

Replacements may also be made by non-natural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89, 9367-9371 and Horwell D C, Trends Biotechnol. (1995) 13, 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g., rat, mouse, bovine and primate cells), may be obtained and such homologues and fragments thereof in general will be capable of selectively hybridizing to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterized sequences. This may be useful where for example silent codon sequence changes are required to optimize codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g., a PCR primer, a primer for an alternative amplification reaction, a probe e.g., labeled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any suitable means available to those of skill in the art. They may also be cloned by standard techniques.

In some embodiments, primers will be produced by synthetic means, involving a stepwise manufacture of the desired nucleic acid sequence one nucleotide at a time. Techniques for accomplishing these automated techniques are readily available in the art.

In some embodiments, longer polynucleotides will generally be produced using recombinant means, for example using a PCR (polymerase chain reaction) cloning techniques. This will involve making a pair of primers (e.g., of about 15 to 30 nucleotides) flanking a region of the target sequence which it is desired to clone, bringing the primers into contact with mRNA or cDNA obtained from an animal or human cell, performing a polymerase chain reaction under conditions which bring about amplification of the desired region, isolating the amplified fragment (e.g., by purifying the reaction mixture on an agarose gel) and recovering the amplified DNA. The primers may be designed to contain suitable restriction enzyme recognition sites so that the amplified DNA can be cloned into a suitable cloning vector.

Hybridization

The present invention also encompasses the use of sequences that are complementary to the sequences of the present invention or sequences that are capable of hybridizing either to the sequences of the present invention or to sequences that are complementary thereto.

The term "hybridization" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridizing to the sequences that are complementary to the subject sequences discussed herein, or any derivative, fragment or derivative thereof.

The present invention also encompasses sequences that are complementary to sequences that are capable of hybridizing to the nucleotide sequences discussed herein.

Hybridization conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical nucleotide sequences while an intermediate (or low) stringency hybridization can be used to identify or detect similar or related polynucleotide sequences.

In some embodiments, the present invention encompasses the use of sequences that are complementary to sequences that are capable of hybridizing under high stringency conditions or intermediate stringency conditions to nucleotide sequences encoding polypeptides having the specific properties as defined herein.

In some embodiments, the present invention encompasses the use of sequences that are complementary to sequences that are capable of hybridizing under high stringency conditions (e.g., 65° C. and 0.1×SSC {1×SSC=0.15 M NaCl, 0.015 M Na-citrate pH 7.0}) to nucleotide sequences encoding polypeptides having the specific properties as defined herein.

The present invention also relates to the use of nucleotide sequences that can hybridize to the nucleotide sequences discussed herein (including complementary sequences of those discussed herein).

The present invention also relates to the use of nucleotide sequences that are complementary to sequences that can hybridize to the nucleotide sequences discussed herein (including complementary sequences of those discussed herein).

Also included within the scope of the present invention is the use of polynucleotide sequences that are capable of hybridizing to the nucleotide sequences discussed herein under conditions of intermediate to maximal stringency.

In some embodiments, the present invention covers the use of nucleotide sequences that can hybridize to the nucleotide sequences discussed herein, or the complement thereof, under stringent conditions (e.g., 50° C. and 0.2×SSC).

In some embodiments, the present invention covers the use of nucleotide sequences that can hybridize to the nucleotide sequences discussed herein, or the complement thereof, under high stringency conditions (e.g., 65° C. and 0.1×SSC).
Biologically Active Preferably, the variant sequences etc. are at least as biologically active as the sequences presented herein.

As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.
Recombinant In some embodiments, the sequence for use in the present invention is a recombinant sequence—i.e., a sequence that has been prepared using recombinant DNA techniques.

These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.
Synthetic In s the sequence for use in the present invention is a synthetic sequence—i.e., a sequence that has been prepared by in vitro chemical or enzymatic synthesis. It includes, but is not limited to, sequences made with optimal codon usage for host organisms—such as the methylotrophic yeasts *Pichia* and *Hansenula*.
Expression of Polypeptides A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.
Expression Vector The term "expression vector" means a construct capable of in vivo or in vitro expression.

In some embodiments, the expression vector is incorporated into the genome of a suitable host organism. The term "incorporated" preferably covers stable incorporation into the genome.

The nucleotide sequence encoding a polypeptide for use in the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g., a plasmid, cosmid, or phage vector will often depend on the host cell into which it is to be introduced.

The vectors for use in the present invention may contain one or more selectable marker genes such as a gene which confers antibiotic resistance e.g., ampicillin, kanamycin, chloramphenicol or tetracycline resistance. Alternatively, the selection may be accomplished by co-transformation (as described in WO 91/17243).

Vectors may be used in vitro, for example for the production of RNA or used to transfect, transform, transduce or infect a host cell.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.
Regulatory Sequences In some embodiments, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e., the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g., promoter, secretion leader and terminator regions.

Preferably, the nucleotide sequence according to the present invention is operably linked to at least a promoter.

Examples of suitable promoters for directing the transcription of the nucleotide sequence in a bacterial, fungal or yeast host are well known in the art.
Constructs The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Organism

The term "organism" in relation to the present invention includes any organism that could comprise a nucleotide sequence according to the present invention or a nucleotide sequence encoding for a polypeptide having the specific properties as defined herein and/or can produce one or more products of interest as described herein.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

Suitable organisms include a prokaryote, fungus yeast or a plant.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a promoter not associated with a sequence encoding a hydrophobia or a membrane protein.

Transformation of Host Cells/Organism

The host organism can be a prokaryotic or a eukaryotic organism.

Examples of suitable prokaryotic hosts include bacteria such as *E. coli* and *Bacillus licheniformis*.

Teachings on the transformation of prokaryotic hosts are well documented in the art, for example see Sambrook et al. (Molecular Cloning: A Laboratory Manual, 2nd edition, 1989, Cold Spring Harbor Laboratory Press). If a prokaryotic host is used then the nucleotide sequence may need to be suitably modified before transformation, e.g., such as by removal of introns.

In another embodiment the transgenic organism can be a yeast.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023. In one embodiment, *T. reesei* is the host organism.

Another host organism can be a plant. A review of the general techniques used for transforming plants may be found in articles by Potrykus (*Annu Rev Plant Physiol Plant Mol Biol* (1991) 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

a. Transformed Fungus

A host organism may be a fungus—such as a filamentous fungus. Examples of suitable such hosts include any member belonging to the genera *Fusarium, Thermomyces, Acremonium, Aspergillus, Penicillium, Mucor, Neurospora, Trichoderma* and the like. In one embodiment, *Trichoderma* is the host organism, preferably *T. reesei*.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus: 50 years on.* Progress in industrial microbiology vol 29. Elsevier Amsterdam 1994. pp. 641-666).

Gene expression in filamentous fungi has been reviewed in Punt et al. *Trends Biotechnol.* (2002); 20(5):200-6, Archer & Peberdy *Crit. Rev. Biotechnol.* (1997) 17:273-306.

b. Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997); 8:554-60.

In this regard, yeast—such as the species *Saccharomyces cerevisi* or *Pichia pastoris* or *Hansenula polymorpha* (see FEMS *Microbiol Rev* (2000 24:45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts*, Vol 5, Anthony H Rose and J. Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al. (1983, *J Bacteriology* 153, 163-168).

The transformed yeast cells may be selected using various selective markers—such as auxotrophic markers dominant antibiotic resistance markers.

A suitable yeast host organism can be selected from the biotechnologically relevant yeasts species such as, but not limited to, yeast species selected from *Pichia* spp., *Hansenula* spp., *Kluyveromyces, Yarrowinia* spp., *Saccharomyces* spp., including *S. cerevisiae*, or *Schizosaccharomyce* spp., including *Schizosaccharomyce pombe*.

A strain of the methylotrophic yeast species *Pichia pastoris* may be used as the host organism.

In one embodiment, the host organism may be a *Hansenula* species, such as *H. polymorpha* (as described in WO 01/39544).

c. Transformed Plants/Plant Cells

A host organism suitable for the present invention may be a plant. A review of the general techniques may be found in articles by Potrykus (*Annu Rev Plant Physiol Plant Mol Biol* (1991) 42:205-225) and Christou (Agro-Food-Industry Hi-Tech March/April 1994 17-27), or in WO 01/16308. The transgenic plant may produce enhanced levels of phytosterol esters and phytostanol esters, for example.

Culturing and Production

Host cells transformed with the nucleotide sequence as described herein may be cultured under conditions conducive to the production of the encoded polypeptide and which facilitate recovery of the polypeptide or product of interest from the cells and/or culture medium.

The medium used to cultivate the cells may be any conventional medium suitable for growing the host cell in questions and obtaining expression of the enzyme.

The protein produced by a recombinant cell may be displayed on the surface of the cell.

The polypeptide may be secreted from the host cells and may conveniently be recovered from the culture medium using well-known procedures.

The product of interest may be secreted from the host cell, it may be displayed on the surface or produce inside the host cell where it may be recovered using well-known procedures.

Secretion

Often, it is desirable for the polypeptide and/or product of interest to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of secretion leader sequences not associated with a nucleotide sequence encoding a lipid acyltransferase in nature are those originating from the fungal amyloglucosidase (AG) gene (glaA—both 18 and 24 amino acid versions e.g., from *Aspergillus*), the a-factor gene (yeasts e.g., *Saccharomyces*, *Kluyveromyces* and *Hansenula*) or the α-amylase gene (*Bacillus*).

Detection

A variety of protocols for detecting and measuring the expression of the amino acid sequence or other products of interest are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J., USA), Promega (Madison, Wis., USA), and US Biochemical Corp (Cleveland, Ohio, USA) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Also, recombinant immunoglobulins may be produced as shown in U.S. Pat. No. 4,816,567.

EXAMPLES

Example 1

Objective: The objective of this experiment was to study the effect of hydrophobin (HFBII) addition to a fed-batch fermentation process using a strain of *Trichoderma* capable of over-producing a hydrolytic enzyme. One control fermentation process was run (no HFBII addition, Run A), to provide baseline data for comparison; another fermentation process was run wherein HFBII was dosed into the reactor vessel (Run B). Dissolved oxygen level, stirrer speed, volumetric oxygen mass transfer, and other parameters related to the culture physiology were monitored for both processes. Airflow rate and backpressure we maintained at constant levels for both tanks. Dissolved oxygen level was maintained at or above 40% relative to saturation at the initial fermentor pressure and temperature by manipulating agitator speed.

DEFINITION OF TERMS kLA: volumetric mass transfer coefficient for oxygen ($h^{-1}$), calculated using the following equation, where OTR is the oxygen transfer rate (mmol $L^{-1}$ $h^{-1}$) and the denominator is the liquid phase concentration of oxygen at equilibrium minus the actual measured liquid phase concentration of oxygen (i.e. the oxygen concentration gradient on the liquid side).

$$k_L A = OTR/(C_{O_2 L}^* - C_{O_2 L})$$

N: stirrer (agitator) speed (rpm)

$P_{Rel}$: relative agitation power (unitless), where N is current agitator speed and $N_i$ is initial agitator speed. $N_i$ for both fermentation processes was the same.

$$P_{Rel} = \frac{N^3}{N_i^3}$$

kLA/$P_{Rel}$: kLA per relative agitation power ($h^{-1}$), a parameter to quantify ease of mass transfer of oxygen that normalizes for differences in relative agitation power input.

$$\frac{\left(\frac{kLA}{P_{Rel}}\right)_B}{\left(\frac{kLA}{P_{Rel}}\right)_A}:$$

Ratio of kLA per relative agitation power ($h^{-1}$) for Run B to Run A (unitless), a parameter to quantify the improvement in kLA per relative agitation power ($h_{-1}$) caused by the addition of HFBII to Run B.

Data & Results

FIG. 1 shows the ratio of kLA per relative agitation power for Run B to Run A (unitless): Data for the first 40% of the run time are not shown because respiration rates during this period are very low and hence introduce excessive noise.

Figure 2:
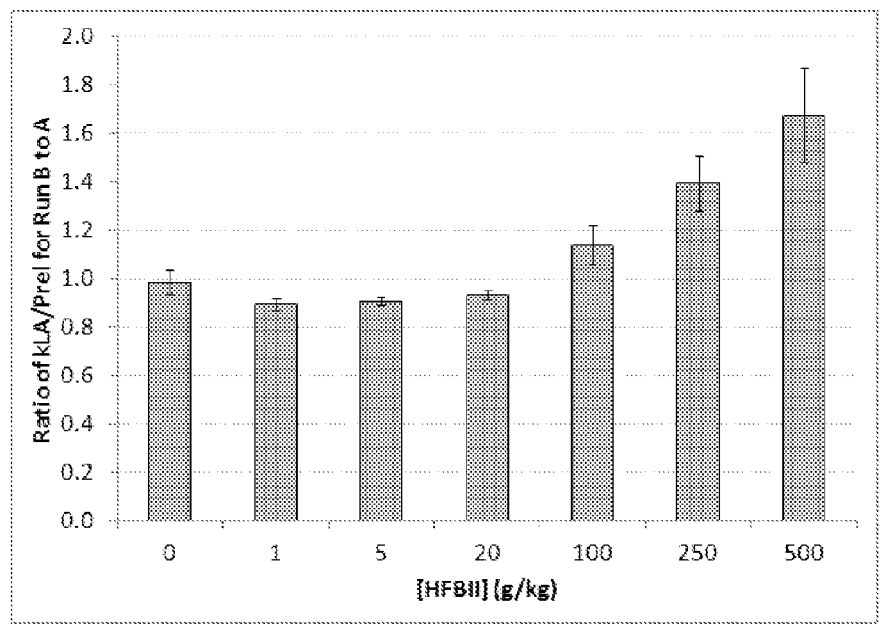
FIG. 2 shows the averaged ratio of kLA per relative agitation power for Run B to Run A as a function of HFBII concentration, ±standard deviation.

FIG. 2 shows the averaged ratio of kLA per relative agitation power for Run B to Run A as a function of HFBII concentration, ±standard deviation.

Summary and Conclusions

Both tanks showed very similar respiration, base addition (nitrogen source) feed rate, carbon source feed rate, dry cell weight, and fermentation broth weight trends, indicating the two fermentation processes were suitable similar to allow comparison and deduce the affect of a single manipulated variable: hydrophobin concentration. Hydrophobin addition to Run B began at a dose of 1 mg/kg. Additional doses of hydrophobin corresponding to cumulative concentrations of 5, 20, 100, 250, and 500 mg/kg were then made. An equivalent volume of sterile water was added to Run A at each addition point.

The effect of HFBII addition to Run B was as follows:
a. The doses of 1, 5, and 20 mg/kg hydrophobin had no observable affect on process data.
b. The doses of 100, 250, and 500 mg/kg hydrophobin caused the ratio of kLA per relative agitation power for Run B to Run A to increase by 14±8%, 40±11%, and 67±19%, respectively.

Example 2

Oxygen Limited (Glucose Excess) *Trichoderma* Growth in Shake Flasks: The purpose of this example is to test whether hydrophobin addition improves oxygen transfer.

*Trichoderma* is grown in shake flasks on a medium with sufficient glucose to ensure the cultures will reach oxygen limitation for a substantial period of time. Test a variety of batched hydrophobin levels up to about 1000 mg/L. Measure dry cell weights (DCW) of cultures at several time points. Since oxygen transfer should be the primary factor limiting growth, it is expected the cultures with more hydrophobin to have higher DCWs since hydrophobin is expected to improve oxygen transfer via enhancement of kLA.

Example 3

Hydrophobin Addition to *Bacillus subtilis* Fermentations: The purpose of this example is to test the effect of hydrophibin in a *Bacillus subtilis* fermentation.

*B. subtilis* fermentation processes have a high oxygen demand for a large fraction of the process time, are grown to high cell mass, and therefore require high levels of agitation and aeration. Thus, these processes would benefit greatly from any kLA enhancement since it would allow reduction in power input and/or facilitate operating the process at even higher cell mass. Run a DO-controlled experiment, similar to Example 1 above, with a control tank and a tank with 500 mg/L batched hydrophobin. Observe any difference in agitation required to maintain dissolved oxygen set point between the two conditions.

Example 4

Hydrophobin Addition to Mammalian Cell Fermentations

The culture of mammalian cells (e.g. Chinese hamster ovary cells for the production of monoclonal antibodies) differs significantly from microbial cells in several important regards: (1) Lower cell densities and lower maximum specific OUR, so much lower volumetric OUR; (2) Lower product concentration (1 vs 10-100 g/kg); and (3) Cells more sensitive to shear and interaction with bubbles, so lower volumetric power input, no Rushtons, and required used of protective non-ionic polymer (e.g. Pluronic F68).

Thus, these processes involving mammalian cells would benefit greatly from any kLA enhancement since it would allow reduction in power input, reduction in stirring rate, and/or facilitate operating the process at even higher cell mass.

The effect of hydrophobin in mammalian cell culture is tested as follows: Chinese hamster ovary (CHO) cells producing a monoclonal antibody are grown according to a standard procedure, for example, the procedure described here http://www.biotechniques.com/multimedia/archive/00074/New Brunswick-FP-Cel 74610a.pdf, which describes a typical protocol for growing CHO cells in a 5.0 L vessel.

In summary, a 2.5 mL vial of CHO cells is thawed and used to inoculate a 125 mL shake flask which contained 25 mL of serum-free CD CHO medium (Invitrogen 10743-029) which is pre-warmed to 37° C. The flask is placed on an orbital biological shaker (NBS Innova® 2000) placed inside a $CO_2$ incubator (NBS Galaxy® 170 R), and set at 120 rpm.

The $CO_2$ incubator is programmed to provide a gas mix of 5% CO2 and 95% air, at 37.0° C. On day 4, when the viable cell density reached 1.5×106 cells/mL, the cells are transferred into a 500 mL shake flask which contained 100 mL of freshly made, pre-warmed medium and allowed to incubate for 3 additional days at the same conditions as earlier. The cells are then transferred to two 1 L shake flasks, each containing 250 mL of the freshly made medium.

The inoculum is grown in the shake flasks until cell density reached $2.0-3.0\times10^5$ cells/mL, with greater than 90% cell viability, sufficient for the bioreactor inoculation.

One day before the cells reached inoculation density, the growth medium is warmed to 37° C. and the Dissolve Oxygen (DO) probe is polarized. For this study, 3.0 L of sterile CD CHO serum-free medium can be prepared by pre-warming at 37° C. for 24 hours in a $CO_2$ incubator. During this time, the DO probe is connected to the controller for at least 6 hours to enable polarization, as per the manufacturer's recommendation.

Once the medium is warmed and the inoculum grown to sufficient starting density, the CelliGen BLU bioreactor is prepared according to the manufacturer's instructions. Next, the vessel containing the cell culture medium is connected to one of the bioreactor vessel's inlet lines using a tube welder.

Several samples are run to test the effect of hydrophobin at different concentrations, e.g., 0, 100, or 500 mg/kg.

In addition the following variables can be tested: (i) Pluronic: 0 or 0.1% w/v, and (ii) Stirring rate: low, mid, high.

All combinations including the different hydrophobin concentrations and variables are tested (6 or more conditions). Cell concentration, cell viability, production concentration, and kLA/oxygenation power are monitored using any suitable method known in the art including those described in the previous examples.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of increasing gas transfer in an aerobic fermentation process comprising adding one or more Class II hydrophobins to a fermentation medium to cause the increase in gas transfer.

2. The method of claim 1, where the gas is oxygen.

3. The method of claim 1, wherein at least one of the one or more Class II hydrophobins is a hydrophobin having a hydrophobin core between 40 and 120 amino acids.

4. The method of claim 1, wherein at least one of the one or more Class II hydrophobins is a hydrophobin fusion protein.

5. The method of claim 1, wherein at least one of the one or more Class II hydrophobins is obtained or obtainable from a filamentous fungus.

6. The method according to claim 5, wherein at least one of the one or more Class II hydrophobins is obtained or obtainable from a fungus of genus selected from the group consisting of *Cladosporium, Ophistoma, Cryphonectria, Trichoderma, Gibberella, Neurospora, Maganaporthe, Hypocrea, Xanthoria, Emericella, Aspergillus, Paracoccioides, Metarhizium, Pleurotus, Coprinus, Dicotyonema, Flammulina, Schizophyllum, Agaricus, Pisolithus, Tricholoma, Pholioka, Talaromyces* and *Agrocybe*.

7. The method of claim 1, wherein at least one of the one or more Class II hydrophobins is generated in situ in the fermentation process.

8. The method of claim 1, wherein said fermentation process has an equilibrium surface tension at a water/air interface below 70 mN/m, or below 50 mN/m, or below 40 mN/m, or below 30 mN/m.

9. The method of claim 1, wherein said fermentation process has a surface shear elasticity at a water/air interface of at least 0.5-0.7 N/m.

10. The method of claim 1, wherein at least one of the one or more Class II hydrophobins is a hydrophobin that causes at least 1 to 2 fold increase in stability of bubbles in the fermentation medium compared to stability of bubbles in the absence of said hydrophobin.

11. The method of claim 1, wherein at least one of the one or more Class II hydrophobins is a hydrophobin that causes at least a 10% increase in the number of bubbles in the fermentation medium compared to the number of bubbles in the fermentation medium in the absence of said hydrophobin.

12. The method of claim 1, wherein at least one of the one or more Class II hydrophobins is a hydrophobin that provides a decrease in an equilibrium surface tension of said fermentation medium below 50 mN/m when compared to the equilibrium surface tension of said fermentation in the absence of said hydrophobin.

13. The method of claim 1, wherein at least one of the one or more Class II hydrophobins is a hydrophobin that causes a surface shear elasticity of said fermentation medium to increase to 0.5-0.7 N/m or higher when compared to the surface shear elasticity of said fermentation medium in the absence of said hydrophobin.

14. The method of claim 1, wherein at least one of the one or more Class II hydrophobins is a hydrophobin that causes a viscous modulus (G"s) of said fermentation medium to increase to 0.02-0.05 N/m when compared to viscous modulus (G"s) of said fermentation medium in the absence of said hydrophobin.

15. The method according to claim 1, wherein at least one of the one or more Class II hydrophobins is a hydrophobin having the general formula:

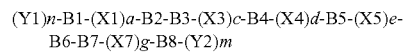

wherein:
m and n are independently an integer between 0 to 200;
B1, B2, B3, B4, B5, B6, B7 and B8 are each an amino acid selected from the group consisting of Cys, Leu, Ala, Ser, Thr, Met or Gly, wherein at least 6 of the residues B1 through B8 being Cys;
a is an integer between 6 to 12;
c is an integer between 8 to 16;
d is an integer between 2 to 20;
e is an integer between 4 to 12; and
g is an integer between 5 to 15.

16. The method according to claim 1, wherein at least one of the one or more Class II hydrophobins is a hydrophobin having the general formula:

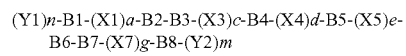

wherein:
m and n are independently an integer between 0 to 10;
B1, B2, B3, B4, B5, B6, B7 and B8 are each an amino acid selected from the group consisting of Cys, Leu or Ser, wherein at least 7 of the residues B1 through B8 being Cys;
a is an integer between 7 to 11;
c is 11;
d is an integer between 4 to 18;
e is an integer between 6 to 10; and
g is an integer between 7 to 10.

17. The method of claim 15, wherein all 8 of the residues B1 through B8 are Cys.

18. The method of claim 15, wherein the group (X3)c comprises the sequence motif ZZXZ, wherein Z is an aliphatic amino acid; and X is any amino acid.

19. The method of claim 15, wherein the hydrophobin is present in a concentration of 0.1-400 µM, or 5-125 µM, or 14-69 µM.

20. The method of claim 15, wherein the hydrophobin is present in a concentration of 50-1000 mg/kg by weight of the total weight of the fermentation medium.

21. The method of claim 15, wherein the hydrophobin is present in a concentration of 0.72-2900 mg/L, or 36-900 mg/L, or 100-500 mg/L.

22. The method of claim 1, wherein said hydrophobin is "HFBII" (SEQ ID NO: 2), or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core thereof.

* * * * *